United States Patent
Stoianovici et al.

(10) Patent No.: US 10,315,046 B2
(45) Date of Patent: Jun. 11, 2019

(54) MULTI-IMAGER COMPATIBLE ROBOT FOR IMAGE-GUIDED INTERVENTIONS AND FULLY AUTOMATED BRACHYTHERAPY SEED

(75) Inventors: Dan Stoianovici, Baltimore, MD (US); Alexandru Patriciu, Ancaster (CA); Dumitru Mazilu, Lutherville, MD (US); Doru Petrisor, Towson, MD (US); Louis R. Kavoussi, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 1222 days.

(21) Appl. No.: 12/085,972

(22) PCT Filed: Dec. 4, 2006

(86) PCT No.: PCT/US2006/046278
§ 371 (c)(1),
(2), (4) Date: Oct. 21, 2009

(87) PCT Pub. No.: WO2007/065013
PCT Pub. Date: Jun. 7, 2007

(65) Prior Publication Data
US 2010/0041938 A1 Feb. 18, 2010

Related U.S. Application Data

(60) Provisional application No. 60/742,170, filed on Dec. 2, 2005.

(51) Int. Cl.
*A61N 5/10* (2006.01)
*A61B 34/30* (2016.01)
(Continued)

(52) U.S. Cl.
CPC ........ *A61N 5/1007* (2013.01); *A61B 10/0233* (2013.01); *A61B 17/3468* (2013.01);
(Continued)

(58) Field of Classification Search
CPC .......................... A61B 19/22–19/2203; A61B 2019/2207–2019/2296
(Continued)

(56) References Cited

U.S. PATENT DOCUMENTS 4,460,826 A * 7/1984 Pryor .......................... 250/227.2
4,719,816 A * 1/1988 Carinas .......................... 74/625
(Continued)

FOREIGN PATENT DOCUMENTS

EP    1 258 908 A2    11/2002
WO   03/047437 A1     6/2003
WO   2004/032760 A2   4/2004

OTHER PUBLICATIONS

Chinzei et al., "MR Compatible Surgical Assist Robot: System Integration and Preliminary Feasibility Study," Int Conf Med Image Comput Assist Interv. Oct. 2000; 3:921-930.
(Continued)

*Primary Examiner* — Catherine B Kuhlman
(74) *Attorney, Agent, or Firm* — Mintz Levin Cohn Ferris Glovsky and Popeo, P.C.; Peter F. Corless

(57) ABSTRACT

Featured is a robot and a needle delivery apparatus. Such a robot comprises a plurality of actuators coupled to control locating any of number of intervention specific medical devices such as intervention specific needle injectors. Such a robot is usable with image guided interventions using any of a number of types of medical imaging devices or apparatuses including MRI. The end-effector can include an automated low needle delivery apparatus that is configured for dose radiation seed brachytherapy injection. Also fea-
(Continued)

tured is an automated seed magazine for delivering seeds to such an needle delivery apparatus adapted for brachytherapy seed injection.

18 Claims, 17 Drawing Sheets

(51) Int. Cl.
*A61B 17/34* (2006.01)
*A61B 10/02* (2006.01)
*A61B 17/00* (2006.01)
*A61B 90/00* (2016.01)

(52) U.S. Cl.
CPC .... *A61B 34/30* (2016.02); *A61B 2017/00544* (2013.01); *A61B 2034/304* (2016.02); *A61B 2090/062* (2016.02); *A61N 2005/101* (2013.01); *A61N 2005/1011* (2013.01)

(58) Field of Classification Search
USPC .................. 600/1–8; 606/130; 74/490.08
See application file for complete search history.

(56) References Cited

U.S. PATENT DOCUMENTS

| | | | | |
|---|---|---|---|---|
| 4,776,749 | A * | 10/1988 | Wanzenberg | B23Q 1/5462 29/39 |
| 5,397,323 | A * | 3/1995 | Taylor | B25J 9/1065 606/130 |
| 5,961,527 | A * | 10/1999 | Whitmore et al. | 606/130 |
| 6,196,081 | B1 * | 3/2001 | Yau | 74/479.01 |
| 6,330,837 | B1 * | 12/2001 | Charles et al. | 74/490.06 |
| 6,418,811 | B1 * | 7/2002 | Rosheim | B25J 17/0266 414/729 |
| 6,638,366 | B2 * | 10/2003 | Lammert et al. | 134/33 |
| 2004/0013509 | A1 * | 1/2004 | Roy | B23Q 1/5462 414/735 |
| 2005/0049486 | A1 * | 3/2005 | Urquhart et al. | 600/429 |
| 2005/0124452 | A1 | 6/2005 | Stoianovici et al. | |

OTHER PUBLICATIONS

Supplementary European Search Report issued in corresponding European Application No. 06848502.8, dated Jan. 16, 2015, 3 pages.

\* cited by examiner

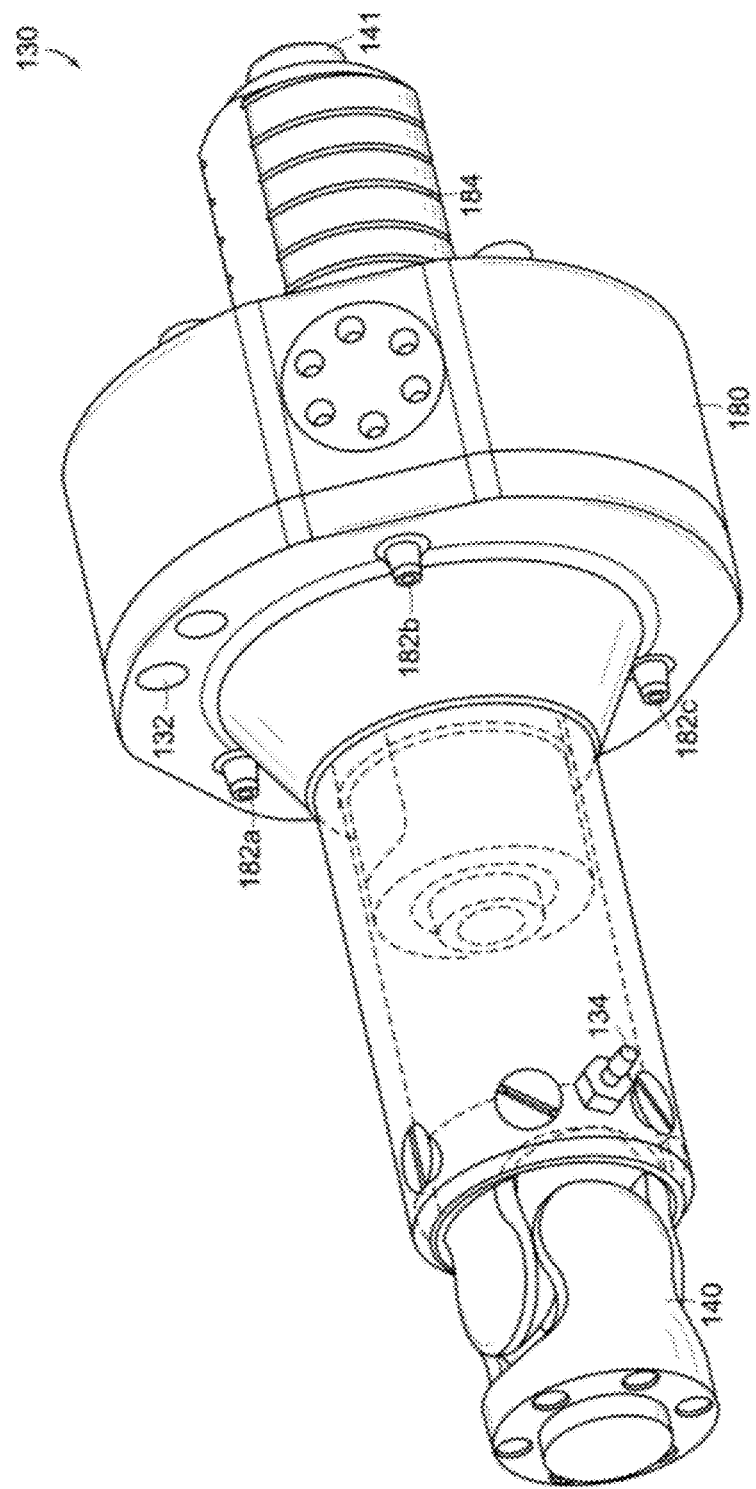

MULTI-IMAGER COMPATIBLE ROBOT FOR IMAGE-GUIDED INTERVENTIONS AND FULLY AUTOMATED BRACHYTHERAPY SEED

This application claims the benefit of U.S. Provisional Application Ser. No. 60/742,170 filed Dec. 2, 2005, the teaching of which are incorporated herein by reference.

STATEMENT REGARDING FEDERALLY-SPONSORED RESEARCH

The present invention was supported by grants from the National Institute of Health (NIH-NCI), grant number CA88232. The U.S. Government may have certain rights to the present invention.

FIELD OF INVENTION

The present invention relates to a robot for medical use, brachytherapy and includes methods, devices and apparatus related thereto and more particularly to such a robot that can be used with any of a number of imaging modalities and/or for image guided interventions, apparatus for automated brachytherapy and including methods, devices and apparatus related thereto.

BACKGROUND OF THE INVENTION

A count of robotics publications in the medical literature reveals that the impact of medical robotics has exponentially grown since its inception in late 1980s. Robots do not only augment physician's manipulation capabilities, but also establish a digital platform for integrating medical information [R. H. Taylor and D. Stoianovici, "Medical robotics in cornputer-integrated surgery," IEEE Transactions on Robotics and Automation, vol. 19, pp. 765-81, 2003; R. M. Satava, "The operating room of the future: observations and commentary," Semin Laparosc Surg, vol. 10, pp. 99-105, 2003}. Medical imaging data, in particular, gives robots abilities unattainable to humans, because, unlike humans, robots and imagers are digital devices. Image-guided interventions (IGI) expand radiology practice above and beyond traditional diagnosis [F. A. Jolesz, "Neurosurgical suite of the future. II," Neuroimaging Clin N Am, vol. 11, pp. 581-92, 2001], and do so with the use of modern tools.

IGI robotic systems, nevertheless, rely on the development of special imager interfaces, image registration, image-guided control algorithms, and also impose stringent requirements on the robotic hardware for imager compatibility, precision, sterility, safety, and nevertheless size and ergonomics. A robot's compatibility with a medical imager refers to the capability of the robot to safely operate within the confined space of the imager while performing its clinical function, without interfering with the functionality of the imager. This depends indeed on the type of intervention and imager used. There is provided in a study [D. Stoianovici, "Multi-Imager Compatible Actuation Principles in Surgical Robotics," International Journal of Medical Robotics and Computer Assisted Surgery, vol. 1, pp. 86-100, 2005], a collection of a set of imager compatibility prescriptions from scientific papers and imager technical notes and assembled a global definition of Multi-Imager Compatibility. The study also derives a compatibility measure for individual imagers and, as expected, found the compatibility with Magnetic Resonance Imaging (to be most demanding.

On the other hand, the potential of MRI guided interventions is significant for the reason that MRI is the method of choice for imaging soft tissue, and, with spectroscopy, is the most advanced imaging modality for tumor detection [F. A. Jolesz, "Neurosurgical suite of the future. II," Neuroimaging Clin N Am, vol. 11, pp. 581-92, 2001; J. Kurhanewicz, M. G. Swanson, S. J. Nelson, and D. B. Vigneron, "Combined magnetic resonance imaging and spectroscopic imaging approach to molecular imaging of prostate cancer," J Magn Reson Imaging, vol. 16, pp. 451-63, 2002]. As such, the integration of robotics with MRI is highly significant for its prospective clinic outcome.

The design and construction of M compatible robots is a very challenging engineering task because most of the components commonly used in robotics can not be used in close proximity of the imager. MRI scanners use magnetic fields of very high density (up to several Tesla), with pulsed magnetic and radio frequency fields. Within the imager, ferromagnetic materials are exposed to very high magnetic interaction forces and heating can occur in conductive materials by electromagnetic induction. The use of electricity also can cause interference which can create image artifacts and/or robot signal distortions. As such, ideal materials for use with MRI are nonmagnetic and dielectric.

The problem becomes more intricate for robot actuation, where the ubiquitous electromagnetic motors are incompatible by principle when using MRI. MRI robotic research to date has commonly utilized piezoelectric (ultrasonic) motors [K Masamune, E. Kobayashi, Y. Masutani, M. Suzuki, T. Dohi, H. Iseki, and K Takakura, "Development of an MRI-compatible needle insertion manipulator for stereotactic neurosurgery," J Image Guid Surg, vol. 1, pp. 242-8, 1995; K. Chinzei and K. Miller, "Towards MRI guided surgical manipulator," Med Sci Monit, vol. 7, pp. 153-63, 2001; E. Hempel, H. Fischer, L. Gumb, T. Hohn, H. Krause, U. Voges, H. Breitwieser, B. Gutmann, J. Durke, M. Bock, and A. Melzer, "An MRI-compatible surgical robot for precise radiological interventions," Comput Aided Surg, vol. 8, pp. 180-91, 2003; D. F. Louw, T. Fielding, P. B. McBeth, D. Gregoris, P. Newhook, and G. R. Sutherland, "Surgical robotics: a review and neurosurgical prototype development," Neurosurgery, vol. 54, pp. 525-36; discussion 536-7, 2004]. These are magnetism free but use high-frequency electricity creating image distortion if operated closer than 0.5 m from the image isocenter. They also require deactivation during imaging.

Pneumatic actuation is a fundamentally flawless option for MRI compatibility. Pneumatics has been used in hand-held drill-like MR instrumentation and tested in MR robotic end-effector designs [J. Neuerburg, G. Adam, A Bucker, K W. Zilkens, T. Schmitz-Rode, F. J. Katterbach, B. Klosterhalfen, E. Rasmussen, J. J. van Vaals, and R. W. Gunther, "MR-guided bone biopsy performed with a new coaxial drill system," Rofo-Fortschr Rontg, vol. 169, pp. 515-520, 1998; E. Hempel, H. Fischer, L. Gumb, T. Hohn, H. Krause, U. Voges, H. Breitwieser, B. Gutmann, J. Durke, M. Bock, and A. Melzer, "An MRI-compatible surgical robot for precise radiological interventions," Comput Aided Surg, vol. 8, pp. 180-91, 2003]. The major limitation of pneumatic actuators, however, has been their reduced precision in controlled motion [H. S. Choi, C. S. Han, K. Y. Lee, and S. H. Lee, "Development of hybrid robot for construction works with pneumatic actuator," Automation in Construction, vol. 14, pp. 452-459, 2005].

While research on MRI compatible robotics has been quantitatively limited, there is a commercial IGI system. Early work [K. Chinzei, N. Hata, F. A. Jolesz, and R.

Kikinis, "MR compatible surgical assist robot: System integration and preliminary feasibility study," *Medical Image Computing and Computer-Assisted Intervention—Miccai 2000*, vol. 1935, pp. 921-930, 2000] was performed at the Brigham and Women's Hospital (BWH), Boston Mass. in collaboration with AIST-MITI, Japan. A robotic surgical assistant was constructed for open MRI presenting five degrees of freedom (DOF) with piezoelectric actuation. The manipulator is located at the top of the imager between the vertical coils of the MRI, and presents two long arms that extend to the imaging region to provide a guide for manual instrument manipulation [K. Chinzei and K Miller, "Towards MRI guided surgical manipulator," *Med Sci Monit*, vol. 7, pp. 153-63, 2001]. Work continues with the development of a one-arm needle support and improved motion accuracy results were reported [Y. Koseki, N. Koyachi, T. Arai, and K. Chinzei, "Remote actuation mechanism for MR-compatible manipulator using leverage and parallelogram-workspace analysis, workspace control, and stiffness evaluation," presented at Robotics and Automation, 2003. Proceedings. ICRA '03. IEEE International Conference on, 2003; Y. Koseki, R. Kikinis, F. A. Jolesz, and K Chinzei, "Precise evaluation of positioning repeatability of MR-compatible manipulator inside M," *Medical Image Computing and Computer-Assisted Intervention—Miccai 2004, Pt 2, Proceedings*, vol. 3217, pp. 192-199, 2004].

An MRI compatible needle insertion manipulator was built at the Medical Precision Engineering lab of the University of Tokyo [K. Masamune, E. Kobayashi, Y. Masutani, M. Suzuki, T. Dohi, H. Iseki, and K. Takakura, "Development of an MRI-compatible needle insertion manipulator for stereotactic neurosurgery," *J Image Guid Surg*, vol. 1, pp. 242-8, 1995]. The system was designed for neurosurgery applications and tested in-vitro. The same group has also designed a neurosurgical micro forceps manipulator [N. Miyata, E. Kobayashi, D. Kim, K. Masamune, I. Sakuma, N. Yahagi, T. Tsuji, H. Inada, T. Dohi, H. Iseki, and K. Takakura, "Micro-grasping forceps manipulator for MR-guided neurosurgery," *Medical Image Computing and Computer-Assisted Intervention-Miccai 2002, Pt 1*, vol. 2488, pp. 107-113, 2002].

A research group from the University of Calgary, Canada also has reported their ongoing work and prototype specifications for the development of an MRI neurosurgical assistant with bilateral arms [D. F. Louw, T. Fielding, P. B. McBeth, D. Gregoris, P. Newhook, and G. R. Sutherland, "Surgical robotics: a review and neurosurgical prototype development," *Neurosurgery*, vol. 54, pp. 525-36; discussion 536-7, 2004].

The Institute for Medical Engineering and Biophysics (IMB), Karlsruhe, Germany. also has reported several versions of a robotic system for breast lesions biopsy and therapy under MR guidance have been developed [W. A. Kaiser, H. Fischer, J. Vagner, and M. Selig, "Robotic system for biopsy and therapy of breast lesions in a high-field whole-body magnetic resonance tomography unit," *Invest Radiol*, vol. 35, pp. 513-9, 2000; A. Felden, J. Vagner, A. Hinz, H. Fischer, S. O. Pfleiderer, J. R. Reichenbach, and W. A. Kaiser, "ROBITOM-robot for biopsy and therapy of the mamma," *Biomed Tech (Berl)*, vol. 47 Suppl 1 Pt 1, pp. 2-5, 2002]. These systems use piezoelectric motors located in a driving unit distal from the high-intensity magnetic field.

A system for general IGI under either computer tomography (CT) or MRI guidance also was developed by the IMB group, utilizing hybrid piezoelectric and pneumatic actuation [E. Hempel, H. Fischer, L. Gumb, T. Hohn, H. Krause, U. Voges, H. Breitwieser, B. Gutmann, J. Durke, M. Bock, and A. Melzer, "An MRI-compatible surgical robot for precise radiological interventions," *Comput Aided Surg*, vol. 8, pp. 180-91, 2003]. This research led to the creation of a spin-off company, Innomedic (Herxheim, Germany, http://innomedic.com/). Innomedic's brochure states that the system is no robot because needle insertion is preformed manually, however, the described system embodies an actuated IGI device with at least 5 DOF of piezoelectric motors and/or pneumatic cylinders. There is no description presently publicly available of the details of such a system.

On the clinical application side, for needle access of the prostate gland under MRI guidance, manual procedures have been experimentally performed in a very few clinical trials, due to the complexity of the MR-IGI and the lack of proper instrumentation. [C. Menard, R. C. Susil, P. Choyke, G. S. Gustafson, W. Kammerer, H. Ning, R. W. Miller, K. L. Ullman, N. Sears Crouse, S. Smith, E. Lessard, J. Pouliot, V. Wright, E. McVeigh, C. N. Coleman, and K Camphausen, "MRI-guided HDR prostate brachytherapy in standard 1.5 T scanner," *Int J Radiat Oncol Biol Phys*, vol. 59, pp. 1414-23, 2004]. Dr. Menard at the NIH (Bethesda, Md.) has investigated the feasibility of IGI for high dose prostate brachytherapy in a closed bore MRI scanner using a needle guide registered to the MRI. Similarly, Drs. D'Amico and Tempany at BWH have performed clinical trials for transperineal biopsy and seed brachytherapy on an open MRI scanner [N. Hata, M. Jinzaki, D. Kacher, R. Cormak, D. Gering, A. Nabavi, S. G. Silverman, A. V. D'Amico, R. Kilinis, F. A. Jolesz, and C. M. Tempany, "MR imaging-guided prostate biopsy with surgical navigation software: device validation and feasibility," *Radiology*, vol. 220, pp. 263-8, 2001]. Finally, a passive needle guide packaged within a custom MR coil was tested on animal models [R. C. Susil, A. Krieger, J. A. Derbyshire, A. Tanacs, L. L. Whitcomb, G. Fichtinger, and E. Atalar, "System for MR image-guided prostate interventions: canine study," *Radiology*, vol. 228, pp. 886-94, 2003] and is presently under clinical trials at the NIH for transrectal prostate biopsy.

It thus would be desirable to provide a new robot that is MRI compatible and preferably compatible for use with any of a number of devices embodying other imaging modalities (e.g., CT, X-ray, etc) and methods for use of such a robot in image guided interventions. It also would be desirable to provide devices, systems, apparatus and methods for automated delivery of a needle and also of brachytherapy seeds.

SUMMARY OF THE INVENTION

The present invention features a robot, a robotic system, needle delivery apparatus that can be use with such a robot as well as methods and devices related thereto. In more particular aspects, such a robot comprises a modular system structure made up of a robotic component that can be adapted for use with any of number of intervention specific medical devices such as intervention specific needle injectors. Such medical devices include, but are not limited to various end-effectors for different percutaneous interventions such as biopsy, serum injections, or brachytherapy. In particular embodiments, such an end-effector is a fully-automated low needle delivery apparatus that is configured for dose radiation seed brachytherapy injection. Also, featured is an automated seed magazine for delivering seeds to such an needle delivery apparatus adapted for brachytherapy seed injection.

Such a robot also is particularly adaptable for use with image guided interventions using any of a number of types of medical imaging devices or apparatuses known to those skilled in the art. In particular embodiments, such a robot is configured for use with Magnetic Resonance Imaging (MRI) devices/apparatuses known to those skilled in the art including those of the highest field strength and such a robot is size accessible within closed-bore tunnel-shaped scanners. In more particular embodiments, such a robot is constructed of materials that are compatible with the working environment associated with MRI. Such materials generally include non-magnetic and dielectric materials such as plastics, ceramics, and rubbers.

Such a robot also is preferably configured so that operation of the functionalities thereof does not involve the use of electricity in proximity to the medical imaging (e.g., MRI) device. In particular embodiments, such a robot utilizes a pneumatic stepper motor for moving the end effector. Such a motor also is generally configured to provide controllable precise and safe pneumatic actuation. In further embodiments, such a robot also embodies fiber optical components so that electrical components such as the control unit for the robot are located outside of the room in which imaging is conducted.

Such a robot is particularly suitable for image-guided percutaneous needle interventions of the prostate in particular for transperineal needle insertion. The prostate is a gland located directly beneath the bladder and completely surrounding the proximal part of the urethra. The robot is particularly designed for transperineal access, because the most direct way to access the prostate percutaneously is through the perineum.

Moreover, because the size of the bore of a closed MRI scanner is on the order of about 500 mm in diameter, the space in such closed bore MRI scanners along the patient is very limited. Previous clinical trials revealed that perineal access legroom may be gained if the patient is positioned in the MRI head first in the left lateral decubitus position (i.e., on his side). As such, the robot of the present invention is configured and arranged so that the patient and the robot can be placed within the bore of an MRI scanner. Since other imager types provide larger access, the arrangement of the robot is acceptable for multi-imager accessibility, but other robot mounting orientations provide versatility of use.

In further aspects embodiments, the present invention features a robot for image-guided interventions that includes a base member, a plurality of actuators coupled to the base member and a platform operably coupled to the platform. The plurality of actuators, the base member and platform are arranged so the platform is moveable with respect to the base member responsive to the plurality of actuators. The plurality of actuators each include a pneumatic stepper motor for moving the platform in a given direction with respect to the actuator.

In further embodiments, the pneumatic stepper motor is a pneumatic rotary stepper motor and the motor includes a plurality of pneumatic ports, where sequential pressurizing of the ports causes a stepping motion. In further embodiments the pneumatic stepper motor includes three ports and the motor is set in stepping motion by sequentially pressurizing the three ports in a 6 step pneumatic commutation process. Such a pneumatic stepper motor further includes a gear head that converts rotary motion of the motor to linear movement along an axis of the actuator. In particular embodiments, the pneumatic stepper motor is that described in PCT/US2006/31030 the teachings of which are incorporated herein by reference.

Such a pneumatic stepper motor also includes a first moving element that is rotated responsive to the motor's stepping motion and a second moving element that engages the first moving element so that the second moving element moves linearly along an axis of the actuator responsive to rotation of the first moving element. In exemplary embodiments, the first moving element is a nut and the second moving element is screw, the nut and screw being configured for linear movement of the screw.

The actuators of such a robot includes a fiber optic encoder for sensing motor operation and a fiber optic limit switch that provides a zero reference for linear movement and the robot further includes fiber optic cables as are known in the art. The fiber optic cables optically interconnect the fiber optic encoder and limit switch to electro-optical interface elements that detects light beam interruptions caused by designated moving elements in the actuator and provide electrical output signals therefrom. The optical cables have a length so that the electro-optical interface elements are located at least a predetermined distance from an imaging device so operation of the electro-optical interference elements at least substantially minimizes, if not avoids, the potential for creating signal interference during the imaging process.

Such a robot further includes a plurality of fluid lines and a plurality of electro-fluidic interface elements, one line and element for each port. Each of the plurality of fluid lines fluidly couples each port to a corresponding one of the plurality of electro-fluidic interface elements that controls coupling and decoupling of each port to a pressurized fluid source. In further embodiments, the robot further includes a plurality of valves fluidly coupled to the pressurized fluid source. The plurality of valves are electrically coupled to the plurality of electro-fluidic interface elements, whereby the interface elements selectively open and close the valves to perform such coupling/decoupling. As with the fiber optic cables, each fluid line has a length so that the plurality of electro-fluidic interface elements are located at least a predetermined distance from an imaging device.

In yet further embodiments, the base member, the platform and the plurality of actuators are arranged and the number of actuators selected so that the platform is supported by the actuators in a five degree of freedom (DOF) parallel linkage structure.

Such a robot also further includes a plurality of support and coupling mechanisms coupled to the base member that maintain the base member in fixed relation, and at a desired orientation with respect, to an imaging device. Such support and coupling mechanisms are configurable so as to be one of removable secured or fixedly secured to the patient support member. Also, such support and coupling mechanisms includes a suction coupling portion that is configured so the suction coupling portion is secured to the patient support member when a vacuum is applied to the suction coupling portion.

In yet further aspects of the present invention, there is featured a robotic system including a robot as described herein and a control unit that is operably coupled to each of the actuators, the control unit being configured to control operation of the robot. In the case where the pneumatic stepper motor is a pneumatic rotary stepper motor and the motor includes a plurality of pneumatic ports, the control unit is configured so as to sequentially pressurize each of the ports so as to cause a stepping motion by the pneumatic rotary stepper motor. Also, when the pneumatic stepper motor includes three ports, the control unit is configured so as to sequentially pressurize each of the three ports in a 6 step pneumatic commutation process.

In the case where the actuator further includes a fiber optic encoder for sensing motor operation and a fiber optic limit switch that provides a zero reference for linear movement, the fiber optic encoder and the fiber optic limit switch are operably coupled to the control unit. Also, in the case where one or more electro-optical interface elements are optically coupled to the fiber optic encoder and limit switch, the one or more electro-optical interface elements are electrically coupled to the control unit so the electrical output signals are inputted to the control unit.

In the case where the robot includes a plurality of electro-fluidic interface elements, each of the plurality of electro-fluidic interface elements is electrically coupled to the control unit. The control unit is configured to control each of the plurality of electro-fluidic interface elements so as to selectively fluidly couple and decouple each port of the stepper motor to a pressurized fluid source so as to thereby sequentially pressurize the ports.

In further embodiments, the control unit includes a microprocessor and an applications program for execution on the microprocessor, the applications program including instructions, criteria and code segments for controlling operation of the robot, more particularly functionalities of the robot. In the case where the pneumatic stepper motor is a pneumatic rotary stepper motor and the stepper motor includes a plurality of pneumatic ports, the applications program includes instructions, criteria and code segments for sequentially pressurizing each of the ports so as to cause a stepping motion by the pneumatic rotary stepper motor. In the case where the stepper motor includes three pneumatic ports, the applications program includes instructions, criteria and code segments for sequentially pressurizing each of the three ports in a 6 step pneumatic commutation process.

In the case, where the robot includes electro-optical interface elements, the applications program includes instructions, criteria and code segments for controlling operation and functionalities of the robot responsive to the electrical output signals. In the case where the robot includes electro-fluidic interface elements, the applications program includes instructions, criteria and code segments for controlling each of the plurality of electro-fluidic interface elements so as to selectively fluidly couple and decouple each port to a pressurized fluid source. In the case where the robot includes support and coupling mechanisms, the applications program includes instructions, criteria and code segments for controlling each of the plurality of support and coupling mechanisms so that the support and coupling mechanisms are selectively coupled to or decoupled from the patient support member. In yet further embodiments, such an applications program includes instructions, criteria and code segments for registering the image and for implementing image-guided control algorithms.

The present invention also features a needle delivery apparatus. Such a needle delivery apparatus includes a needle, a housing having an interior chamber extending lengthwise and an outlet, and a pneumatic stepper motor coupled to the housing and disposed in the interior chamber. As further described herein, such a needle delivery apparatus is adapted for injecting brachytherapy seeds.

Such a needle delivery apparatus also includes a first interior member having an interior chamber extending lengthwise and a piston moveably disposed in the first interior member chamber (hereinafter the needle piston), where the needle piston is coupled to the needle. The first interior member is operably coupled to the pneumatic stepper motor and configured so that operation of the pneumatic stepper motor causes the first interior member to move lengthwise within the housing interior chamber and with respect to the housing.

The first interior member chamber and the needle piston are configured so that when pressurized fluid (e.g., gas) is admitted in one variable end portion of the first interior chamber, that is opposite to the needle piston, the needle moves in a first direction. Also, when fluid is removed from the one variable end portion of the first interior chamber so as to create a negative pressure therein, the needle moves in a second direction opposite to the first direction. The length of the first interior member chamber is set so a first end of the first interior member chamber defines a stop for the needle piston so as to thereby limit movement of the needle in the first direction.

In alternative embodiments, the first interior member and piston are configured so that operation of the piston in either the first or second directions results by at least admitting pressurized fluid (e.g., gas) into the first interior chamber on one side of the needle piston thereby causing movement of the piston in the desired direction. Also, the first interior member and piston are configurable so that a resilient member is operably coupled to the piston and the first interior member or other structure thereof such that it applies a force to the needle piston to restore the piston to a desired location within the first interior member chamber. For example, a spring like element or resilient member is disposed within the first interior chamber between the first end thereof and the needle piston so it is compressed there between when the needle piston moves in the first direction. Also, such a member can be element can be disposed between a second end of the first interior member chamber and the needle piston so it extends there between when the needle piston moves in the first direction. In this way, the spring like element or resilient member applies a force that moves the needle piston in the second direction. It also should be recognized that combinations of the above described structures are contemplated and thus within the scope of the present invention.

The needle delivery apparatus further includes a second interior member and a second end of the first interior member includes a through aperture therein. The second interior member is movably within the first interior member, in particular the first interior member chamber and one end of the second interior member is coupled to the needle piston. A portion of the second interior member, including a second end thereof extends outwardly through and from the through aperture in the first interior member second end. As the second interior member is coupled to the needle piston, the second interior member moves within the first interior member chamber responsive to the above described movement of the needle piston in the first and second directions.

The second interior member also includes a stylet and a chamber that extends lengthwise therein and the needle piston further includes a through aperture therein. The stylet is movably (e.g., slidably) disposed with the needle piston through aperture. The stylet extends lengthwise in the second interior member chamber, through the needle piston through aperture and through a lumen in the needle. The apparatus also includes a piston moveably disposed in the second interior member chamber (hereinafter the stylet piston), the stylet being coupled to the stylet piston.

The second interior member chamber and the stylet piston are configured so that when pressurized fluid (e.g., gas) is admitted in one variable end portion of the second interior member chamber, that is opposite to the styley piston, the stylet moves in the first direction within the first interior chamber. They also are configured so that the stylet moves in the second direction opposite to the first direction when the fluid is removed from the one variable end portion of the second interior member chamber so as to create a negative pressure therein. In further embodiments, the length of the second interior member chamber is set so that when a negative pressure is created in the one variable end portion of the second interior member chamber, the stylet is withdrawn through the needle lumen thereby defining an open channel in the lumen that extends from an open end of the needle to an end of the stylet. As indicated above regarding the first interior member, the foregoing method for moving the stylet piston is not limiting and other techniques and devices are usable to move the stylet piston in the second direction.

In further embodiments, such a needle delivery apparatus further includes a delivery mechanism that is operably coupled to a lumen of the needle, so that material can be delivered to the lumen and thence through the lumen to tissue surrounding an open end of the needle disposed in the tissue. The material being delivered includes medicaments, tissue, antibiotics, markers and seeds, the seeds including one of medicaments or radioactive material. In yet further embodiments, the needle delivery apparatus includes a control unit for controlling the delivery apparatus, more particularly functionalities of the delivery apparatus including controlling operation of the stepper motor and movement of the pistons.

In yet further embodiments, such a needle delivery apparatus further includes a seed delivery mechanism. Such a seed delivery mechanism includes a delivery line fluidly coupled to a source of seed and the needle delivery apparatus; and a seed delivery pressure source fluidly coupled to the delivery line that pressurizes the delivery line so as to cause the seed to pass through the delivery line into the needle delivery apparatus. After the seed is delivered to the needle delivery apparatus it is moved within the needle delivery apparatus so as to be disposed within the needle lumen.

In more particular embodiments, the needle delivery apparatus control unit is configured to control movement of the stylet piston in the first or second directions. Thus, when a seed is to be loaded into the needle lumen, the control unit causes the stylet to move in the second direction through the needle lumen past the seed delivery point (e.g., creating an open lumen), whereby the seed can be moved into the lumen. When the seed is to be dispensed from the needle into tissue, the control unit causes the stylet to move in the first direction back through the needle lumen thereby pushing the seed through the needle lumen and thence out the open end of the needle into the tissue.

The control unit is further configured to control operation of the stepper motor so as to cause the open end of the needle to move in one of the first or second directions. Also, such control by the control unit causes the stepper motor to generally move the first interior member in one of the first or second directions so as to thereby move the open end of the needle to another location. For example, the open end of the needle is movable in a second direction from one location to another location, whereby another seed can be delivered to the another location.

In yet further embodiments, the seed delivery mechanism includes a plurality of delivery lines, each delivery line being fluidly coupled to a seed source having seeds with different properties. The plurality of delivery lines are configured and arranged so as to form a single delivery line portion that is fluidly coupled to the needle delivery apparatus and thus to the needle lumen. The seed delivery pressure source is fluidly coupled to each of the plurality of delivery lines that pressurizes each delivery line. In this way, a seed having a desired property passes through the delivery line corresponding to the selected source of seed, through the single delivery line portion into the needle lumen.

In yet further embodiments, the seed delivery mechanism further includes one or more seed sensors, one for each delivery line. Each of the one or more seed sensors is configured to detect passage of each seed through a corresponding delivery line and to output a seed detection signal. The control unit is operably coupled to each of the one or more seed sensors and is configured so to count the seeds passing through each delivery line responsive to the outputted seed detection signal.

In more particular embodiments, each of the one or more seed sensors is an optical sensor and the needle delivery system further includes one or more fiber optic cables and one or more additional electro-optical interface elements, where the one or more fiber optic cables optically couple the one or more seed sensors and the one or more additional electro-optical interface elements. Each of the one or more electro-optical interface elements provides an electrical output signal to the control unit responsive to the outputted seed detection signal.

Also featured are methods embodying such devices, robots, systems and apparatus of the present invention as described herein.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 1 is an illustrative view of a robot of the present invention in an MRI intervention setup, with an end effector and without interconnecting cable and fluid lines for clarity;

FIG. 2(*a*) is a perspective schematic view of an illustrative robot of the present invention configured for support from the base of the robot;

FIG. 2(*b*) is a perspective schematic view of an illustrative robot of the present invention configured for support from a side of the robot;

FIG. 3 is a perspective view of a pneumatic linear actuator;

FIG. 4 is a perspective view of the pneumatic motor embodied in the actuator of FIG. 3 and the needle delivery apparatus of FIG. 6(*a*)-(*b*);

FIG. 5(*a*) is a perspective view of an illustrative needle delivery apparatus of the present invention;

FIG. 5(*b*) is a cross-sectional schematic view of the needle delivery apparatus of FIG. 6(*a*);

FIG. 5(*c*) is a partial cross-sectional view of the first interior member illustrating an alternative embodiment for moving the piston;

FIG. 5(*d*) is a partial cross-sectional view of the first interior member illustrating yet another alternative embodiment for moving the piston;

FIG. 6 is an illustrative schematic view of a seed delivery apparatus according to the present invention;

FIG. 7 is a schematic perspective view of a portion of an end effector with image registration markers;

FIG. 8(*a*) is a schematic block diagram view of a robotic system of the present invention with one channel illustrated for clarity;

FIG. 8(b) is a schematic block diagram view of a needle delivery system of the present invention configured for seed injection;

DESCRIPTION OF THE PREFERRED EMBODIMENT

Figure 1:
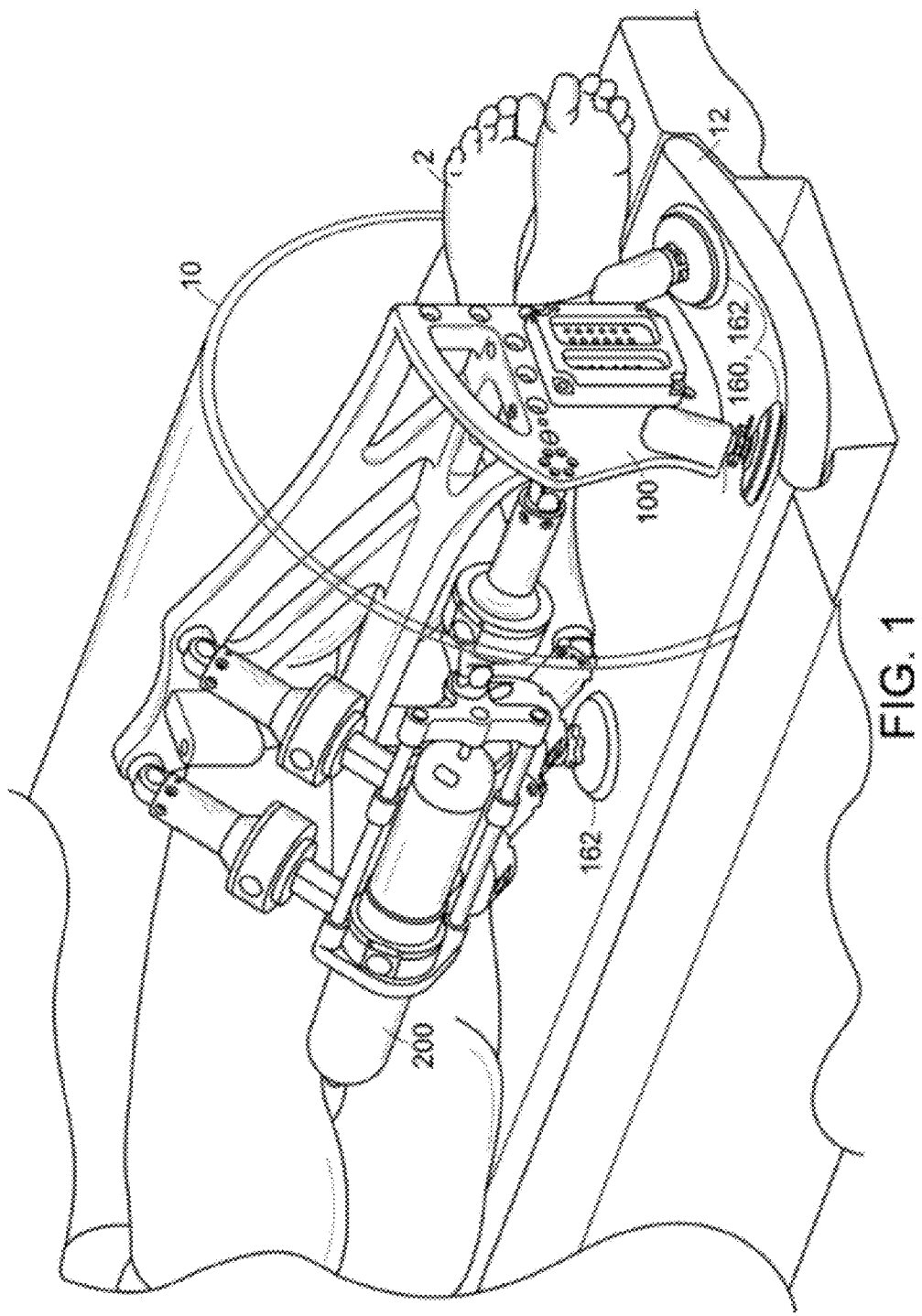

The present invention features a robot, a robotic system, needle delivery apparatus that can be used with such a robot as well as methods and devices related thereto. In more particular aspects, such a robot generally includes a modular system structure that can be adapted for use with any of number of intervention specific medical devices such as intervention specific needle injectors. Such medical devices include, but are not limited to various end-effectors for different percutaneous interventions such as biopsy, serum injections, or brachytherapy. As also described herein, in particular embodiments such an end-effector is a fully-automated low dose radiation seed brachytherapy injector. Additionally, the present invention includes an automated seed magazine for delivering seeds to such a seed brachytherapy injector. Thus, in an all inclusive aspect, a robotic system of the present invention includes all of the foregoing features.

Such a robot also is particularly adaptable for use with image guided interventions using any of a number of types of medical imaging devices or apparatuses known to those skilled in the art. In particular embodiments, such a robot is configured for use with Magnetic Resonance Imaging (MRI) devices/apparatuses known to those skilled in the art including those of the highest field strength and is size accessible within closed-bore tunnel-shaped scanners.

In more particular embodiments, such a robot is constructed of materials that are multi-imager compatible. In this regard, multi-imager compatible shall be understood to generally mean the capability of the robot, including the materials of the robot, to safely operate within the confined space of the imager while performing its clinical function, without interfering with the functionality of the imager or the imaging process (e.g., MRI, CT, X-ray, etc.). In more specific embodiments, such materials includes nonmagnetic and dielectric materials such as plastics, ceramics, and rubbers. In yet more specific embodiments, such materials include but are not limited to Polyetherimide (Ultem 1000), Delrin, Nylon 6/6, Peek 1000, Garolite G-11, Polyimide, high-alumina ceramic, glass, sapphire, PTFE (Teflon), Silicone rubber, which have been generally shown to be multi-imager compatible.

The following discussion describes the robots and robotic systems of the present invention with reference to image-guided percutaneous needle interventions of the prostate in particular for transperineal needle insertion as the robot of the present invention is particularly suitable for image-guided percutaneous needle interventions of the prostate in particular for transperineal needle insertion. The prostate is a gland located directly beneath the bladder and completely surrounding the proximal part of the urethra. The gland is walnut-shaped and measures about 40×30×30 mm. Depending on the amount of subcutaneous tissue, in most men the center of the prostate lies about 70±20 mm beneath the perineal skin.

Clinical specifications also impose motion requirements and predilections for the injector and needle deployment. Traditionally, transperineal needle insertion for prostate access has been performed (under different imaging modalities, most commonly transrectal ultrasound) with a template of uniformly distributed holes, used to guide the needles during manual insertion. A robot of the present invention allows for a similar range of translational motion (50×50 mm), but can achieve much finer positioning capability (0.5 mm versus 5.0 mm typically on the template). Unlike the manual access case, the robot of the present invention can slightly orientate the injector (e.g., ±10°) so that specific anatomical structures (i.e., pubic bone, urethra for prostate access) are more easily avoided. In more particular embodiments, the speed of the robot is limited to about 20 mm/sec and the robot and system thereof are configured so as to provide a fail-safe non-backdrivable actuation. However, the speed of the needle is not necessarily restricted to the above speed for needle insertion to minimize soft tissue deflections during insertion.

Although the following discussion refers to image-guided percutaneous needle interventions of the prostate, this shall not be considered limiting. It is within the scope of the present invention for the end effector used with the robot to be configured and arranged to perform any of a number medical procedures or techniques known or hereinafter developed by those skilled in the art which lend themselves to use of the robot including percutaneous interventions such as biopsy, serum injections, or brachytherapy. Also, although the robot described herein is particularly designed for transperineal access, because the most direct way to access the prostate percutaneously is through the perineum; this shall not be considered limiting. The structure and arrangement of the robot including the functionalities thereof, is adaptable so the robot can be used with any of a number medical procedures or techniques known or hereinafter developed by those skilled in the art which lend themselves to use of the robot of the present invention. Such often procedures/techniques, includes those where there is grinding or milling of bone or the skeletal structure.

Figure 2A:
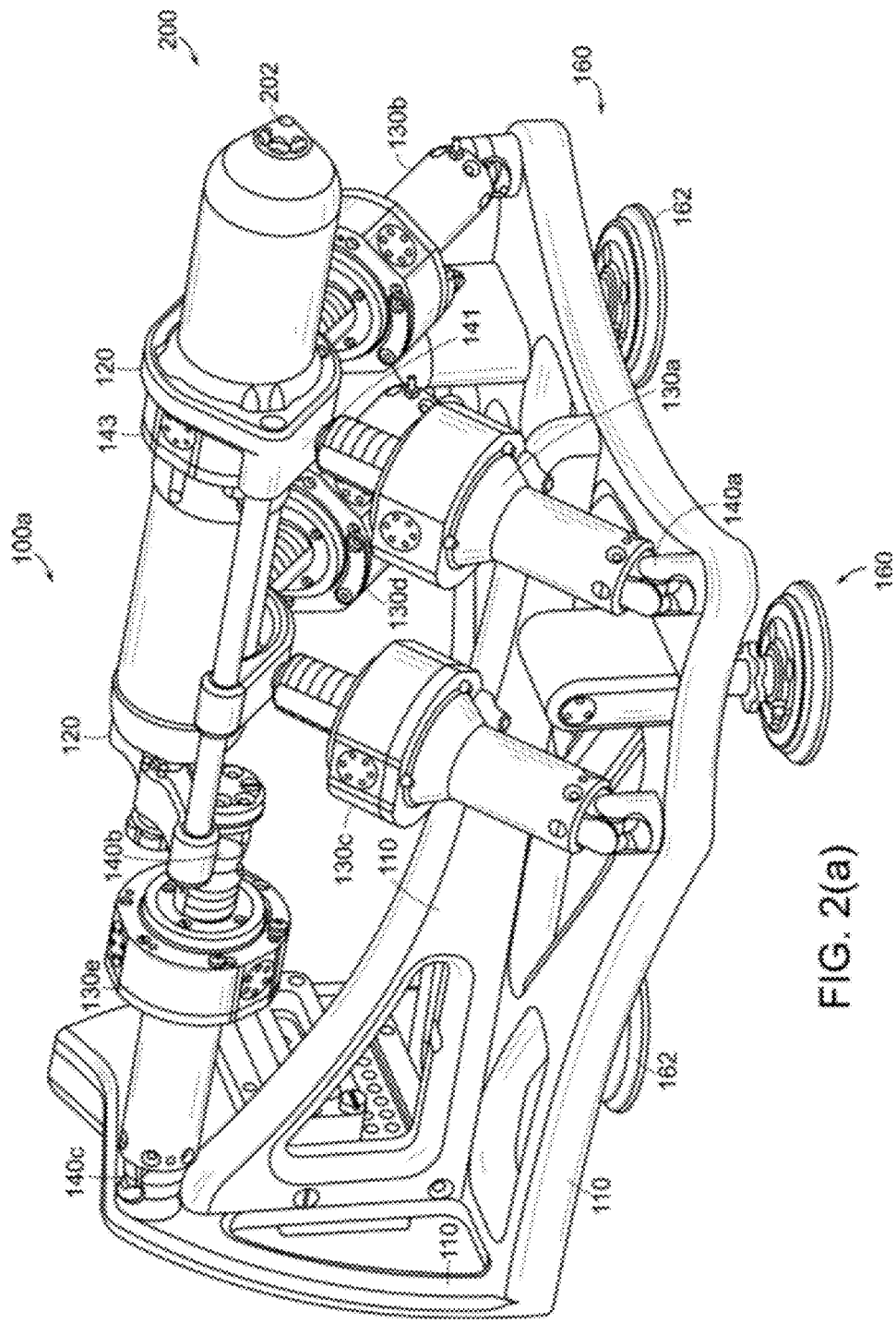

Thus and referring now to the various figures of the drawing wherein like reference characters refer to like parts, there is shown in FIG. 1 various illustrative views of a robot 100 of the present invention in an MRI intervention setup, where the view shown in FIG. 1 is without interconnecting fiber optic cables and fluid lines for clarity. There also is shown in FIGS. 2(a), (b) a perspective schematic view of an illustrative robot of the present invention with an end effector 200 when configured for support from the base of the robot 100a (FIG. 2(a)) and when configured for support from the side of the robot 100b (FIG. 2(b)). Reference numeral 100 is used when referring to the robot generally, however, when referring to any one or more specific robotic configurations, the reference numeral is followed by an alpha character or letter (e.g., 100a).

As shown in FIG. 1, the robot 100 with the end effector 200 and the patient 2 or subject are placed within the bore of an MRI scanner 10. Because other imager types provide larger access than that typically available for MRI scanners, the arrangement is acceptable for multi-imager accessibility, but other robot mounting orientations provide versatility of use. As also illustrated in FIG. 1, the robot 100 is mounted or disposed on structure of the MRI scanner 10 so that the robot is generally maintained in fixed relation to the MRI scanner during the imaging process. In a particular illustrative embodiment, the robot 100 is removably secured to a patient platform 12 on which the patient 2 is placed during the imaging process.

Such a robot 100 includes a base 110, a platform 120 and a plurality of linear actuators 130 that are operably coupled to the base. Reference numeral 130 shall be used when referring to the linear actuators generally, however, when referring to any one or more specific actuators, the reference numeral is followed by an alpha character or letter (e.g., 130a). In the illustrated embodiment, the robot 100 is constructed so the platform 120 is supported by articulated linear actuators 130a-e in a 5 degree of freedom (DOF) parallel linkage structure, such as that shown more clearly in FIGS. 2(a),(b). The architecture and sizing of the parallel link structure is established considering motion specifications, space constrains of the MRI, and patient positioning in iterative kinematic analysis and IGI simulation. The number and arrangement of the linear actuators 130 shall not be considered as being limiting as it is within the skill of those knowledgeable in the art to adjust the arrangement and number of linear actuators to achieve any of a number of supporting structures known to those in the art.

In particular exemplary embodiments, the platform is supported by five linear actuators 130a-e. The back actuator 130e is operably connected to, and between, the base 110 and the platform 120 by two (2) universal joints 140b,c. Their role is to prevent the rotation of the platform 120 about the axis of a needle (e.g., like a constant velocity axel). The other four actuators 130a-d are operably coupled to the base 110 by U-joint connections 140a and spherical joints 141 at the platform side. The actuators 130 preferably are linear type of actuators so they do not rotate. As described further below, each of the actuators 130 is fluidly coupled to one or more fluid lines 170 (FIG. 5) for actuation of the actuator and is optically coupled to one or more fiber optic cables 172 for sensing operational conditions or parameters.

The injector end-effector 200 attaches coaxially to the platform 120. In the illustrated embodiment, the injector end-effector 200 houses a needle 202. However, it should be recognized that end-effectors 200 depend on the specifics of the IGI, normally involving multiple DOF.

Such a robot structure presents 6 position-controlled DOF, with two redundant translations in the direction of the needle 202. Rotation about the axis of the needle is blocked since it is generally irrelevant for the IGI (needle symmetry). It is within the scope of the present invention and the skill of those knowledgeable in the art, to adapt the robot of the present invention to allow rotation about the needle axis. The two redundant translations are used for the initial positioning of the injector and subsequently for needle insertion. Three translational DOF (X, Y, Z) and 2 rotations (X, Y) are available for controlled positioning of the injector.

In further embodiments and as described in detail hereinafter, the needle 202 is actuated by a pneumatic piston whose cylinder is precisely positioned with another linear actuator 143. As such, the depth of insertion is always at the end-of-stroke, but this limit is shifted with the entire cylinder before the insertion. Such an arrangement allows for very fast (pressure regulated) yet precise needle insertions. Additional DOF may be provided for special end-effectors (e.g., seed loading) but these are typically in the form of pneumatic cylinders.

Figure 2B:
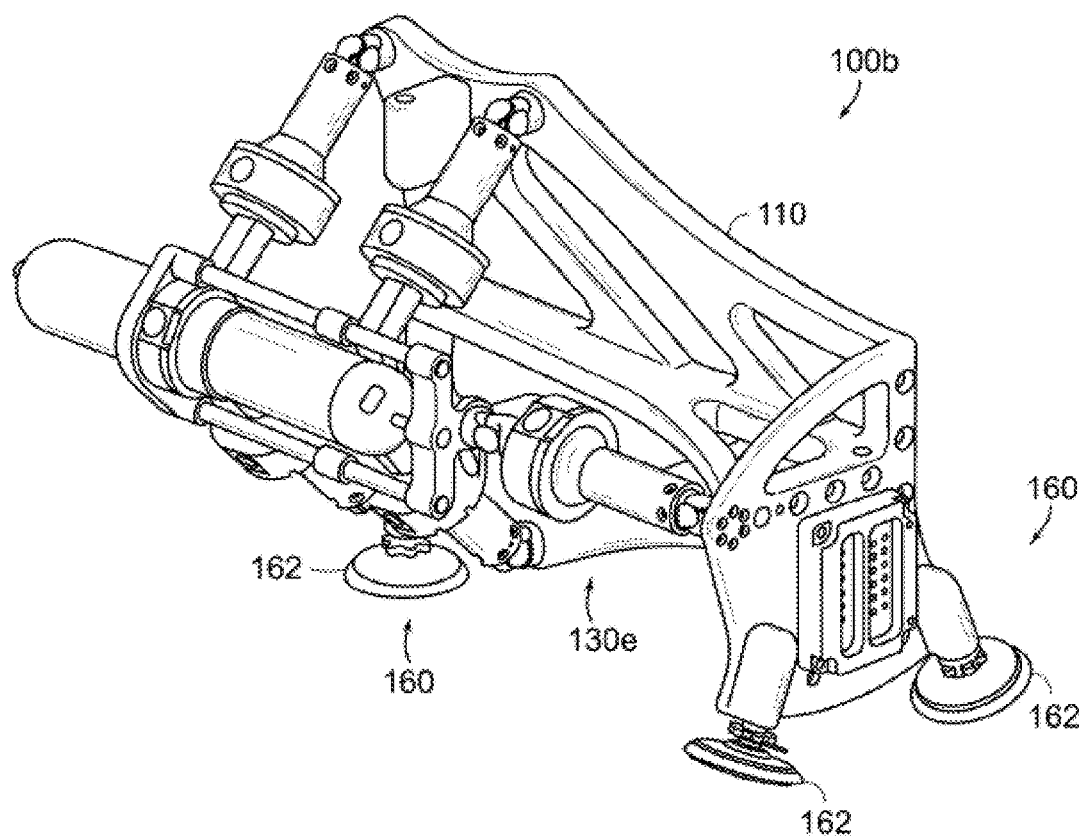

Depending on the clinical intervention and the type of imager being used, the robot may be mounted on its side as illustrated in FIGS. 1 and 2(b), or horizontally as represented in FIG. 2(a). In either case, the base 110 or frame of the robot 100 is preferably secured to a table of the imager (e.g., patient platform 12) using any of a number of support and coupling mechanisms 160 known to those skilled in the art. In exemplary embodiments, such a support and coupling mechanism is formed of a plurality of suction cup structures 162, more specifically three such structures that are mounted on the proper side of the base. For example, a side surface of the base 110 as shown in FIG. 1 or the bottom surface as shown in FIG. 3. Such suction cup structures 162 are coupled to a vacuum source via tubing 163 (FIG. 8(a)) and are thereby activated by the vacuum source. In further embodiments, such a vacuum source is remotely located from the robot 10 such as for example in control room where the imaging process is controlled from. As also illustrated in FIG. 2(b), the support and coupling mechanisms can 160 be arranged so that the robot 110b is supported from either side of the robot.

Figure 4:
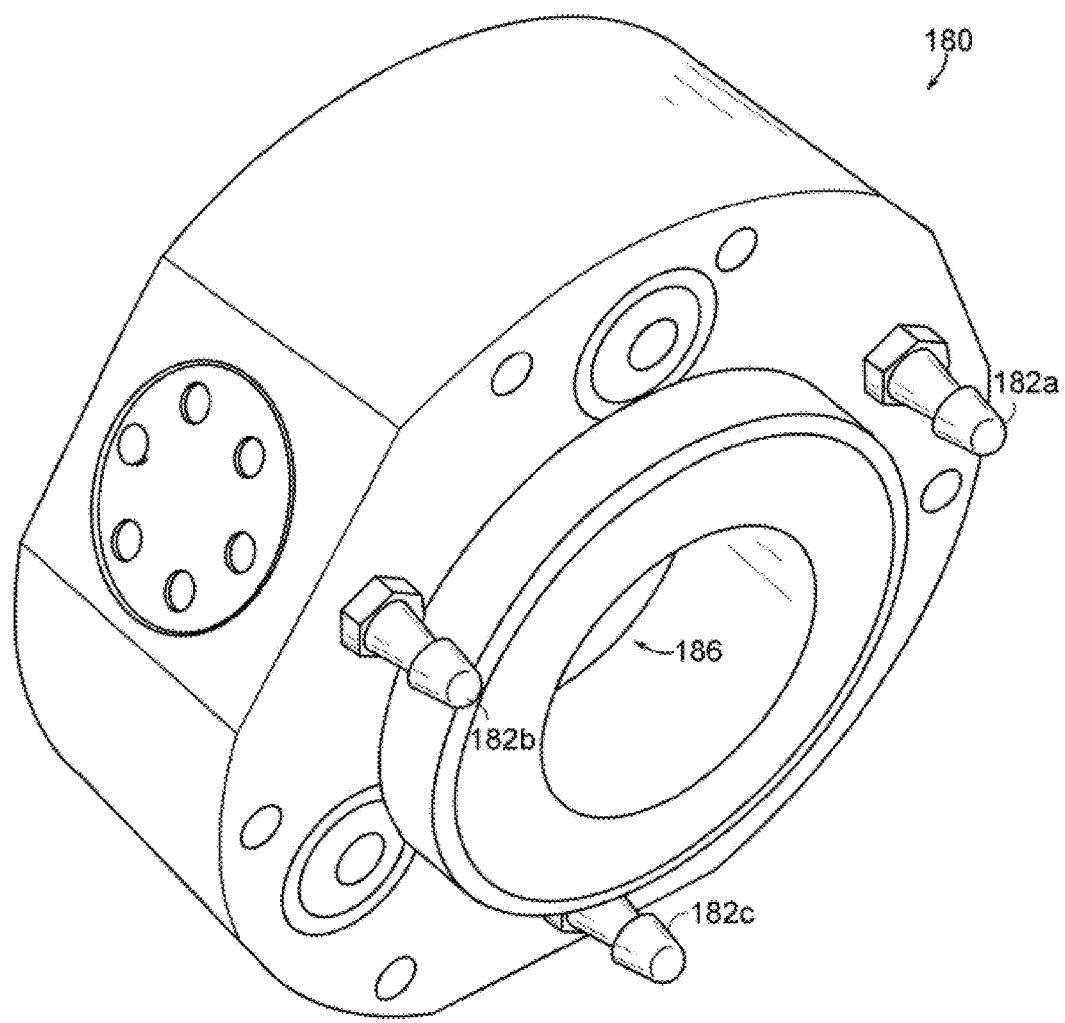

Referring now to FIGS. 3-4 there is shown a perspective view of a linear actuator 130(FIG. 3) and a perspective view of a pneumatic motor 180 embodied in such an actuator (FIG. 4). Reference shall be made to PCT/US2006/31030 (having as least one inventor in common), the teachings of which are incorporated herein by reference for further details and characteristics of the pneumatic motor 180 not otherwise described herein. In preferred embodiments, the motor 180 and linear actuator 130 are pneumatically actuated as it is believed (without reliance upon any particular theory) that pneumatic actuation is particularly suitable for medical environments and imager compatibility. The gaseous material used for actuation is air or any gas that is otherwise appropriate for the intended use. This preference shall not be limiting, however, as the motor and actuator can be adapted for use with fluids that are otherwise appropriate for the intended imaging use.

The motor 180 is a pneumatic stepper motor that provides controllable motion with fail-safe operation) and includes a plurality of ports 182 (hereinafter pneumatic ports 182). In more specific embodiments, the motor includes three pneumatic ports 182a-c. Step motion of the motor 180 is achieved by sequentially pressurizing the ports 182a-c (i.e., pneumatic commutation). The output of the motor 180, which presents a central bore, includes a central nut 186 engaging a screw 184 for linear actuation. In exemplary embodiments, the linear size of the motor step is 0.083 mm and the max speed is 16.6 ml/s. The actuator presents fail-safe operation because in case of malfunction it may only lock, and is non-backdrivable.

The motor 180 also encases a special gearhead and a custom fiber optic quadrature encoder including optical ports 132 for closed-loop control or redundant sensing in open-loop stepper operation. A fiber optic limit switch also is provided at one end of the linear travel with an optical port 134 that provides the zero reference for linear motion. For full MRI compatibility both sensors, the motor's quadrature encoder and the limit switch, are implemented at the end of the fiber optic cables 172 (FIG. 2), so that the robot 100 is electricity free. These optic circuits sense light beam interruptions caused by designated moving elements in the actuator.

Figure 5A:
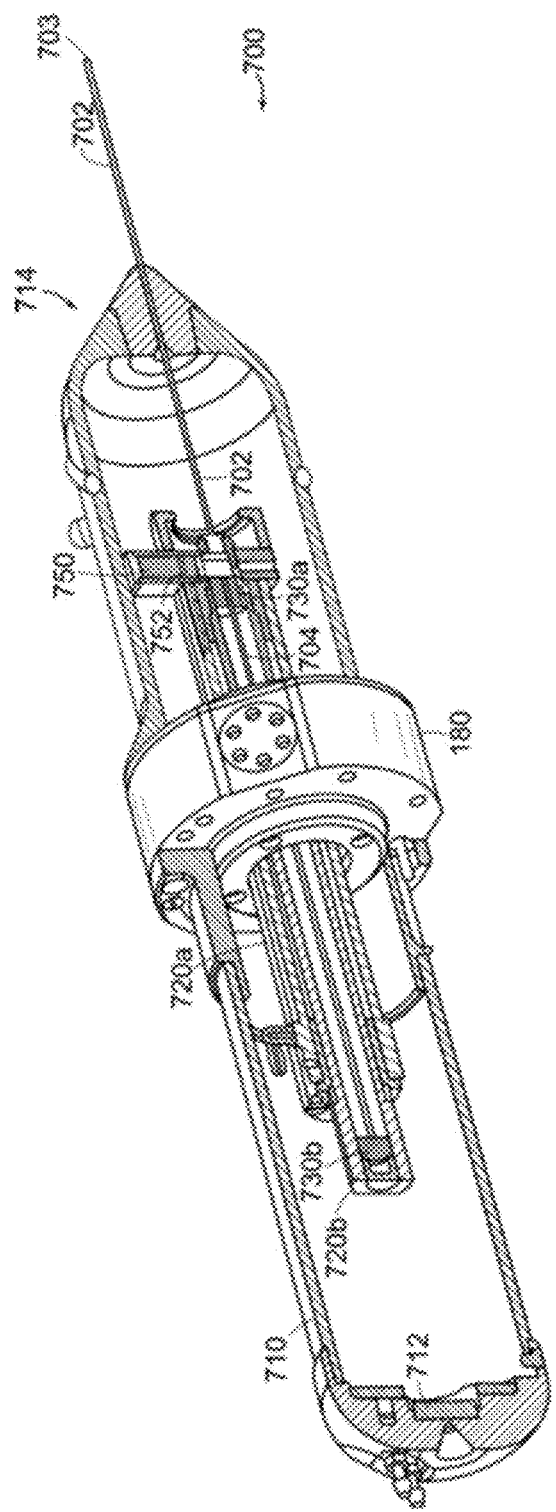
Figure 5B:
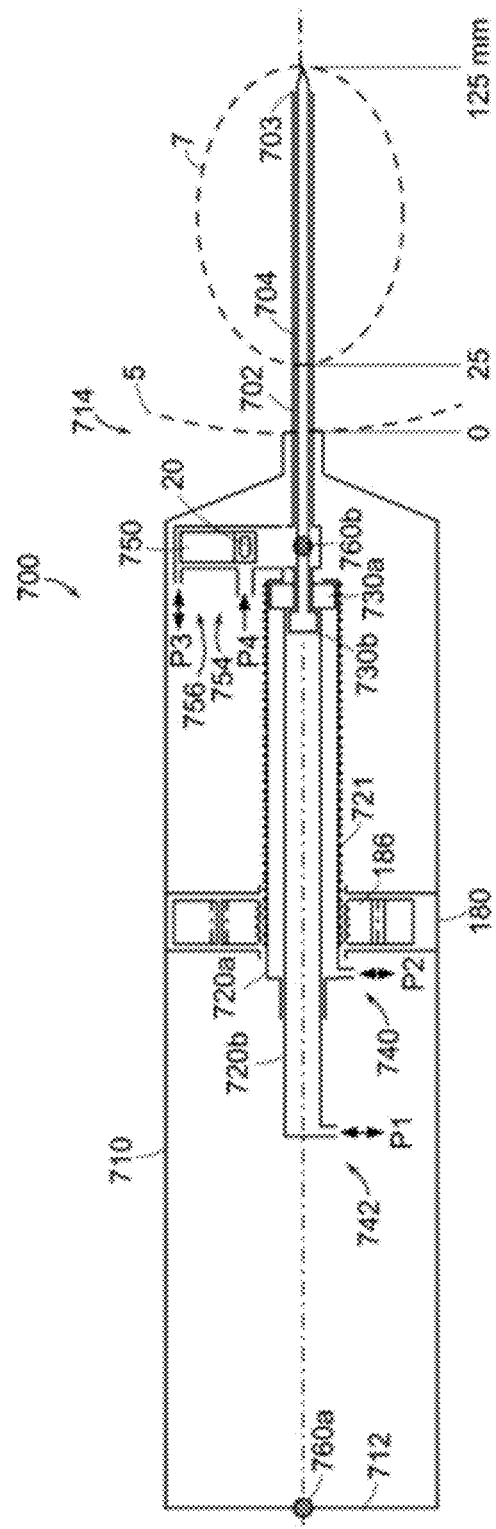
Figure 5C:
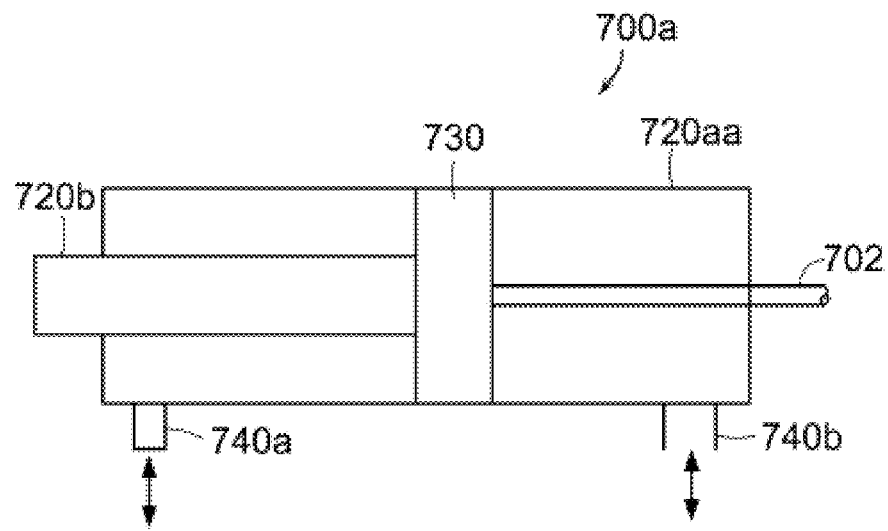
Figure 5D:
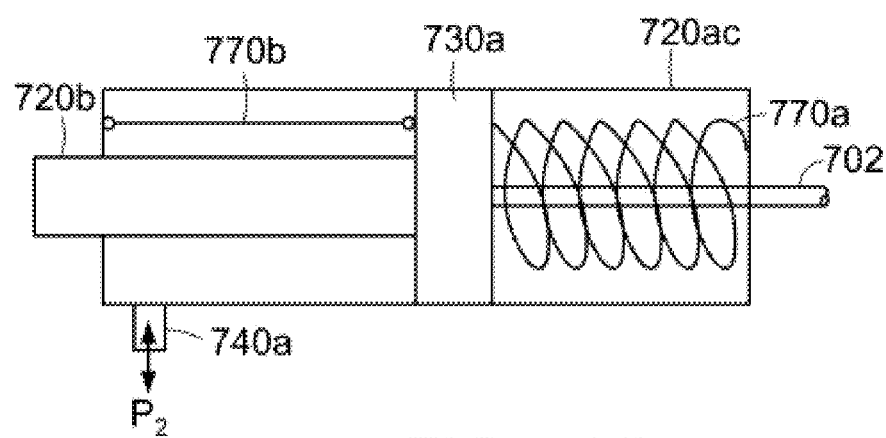

Referring now to FIGS. 5(a)-(b), there are shown various views of an illustrative needle delivery apparatus 700 of the present invention. The design of the needle delivery apparatus 700 was based on a series of ex-vivo experiments of needle insertion which were performed in various animal organs under x-ray. These experiments generally confirmed that needle insertion accuracy, soft tissue deflection, and needle bending can be minimized by performing a quick insertion of the needle. This is in fact what a number of physicians try to perform by hand.

In general in the present invention, the orientation of the needle 702 is precisely set by the robot 100 and the depth of insertion is exactly set with a pneumatic motor 180. A pneumatic cylinder is then employed to insert the needle. The illustrated needle delivery apparatus 700 also is configurable for injection of brachytherapy seeds. Thus, the needle delivery apparatus 700 further includes a seed deployment and reloading mechanism 750. As with the robot 100, the needle delivery apparatus 700 of the present invention is arranged and uses materials such that the needle delivery apparatus preserves multi-imager compatibility, which is an electricity see, dielectric, and nonmagnetic property. The needle delivery apparatus 700 is supported by the robot 100, which shifts the skin entry point similar to choosing another hole of the brachytherapy template in the manual procedure, however, the present invention is not limited to the 5 mm grid of the template. In contrast to the template case, the orientation of the needle 702 can be adjusted from one insertion site to another with the present invention.

Such a needle delivery apparatus 700 of the present invention includes a case 710, a pneumatic motor 180 (like that used in the robot actuator 130), first and second pneumatic cylinders 720*a,b*, a needle 702, and a stylet 704. The case 710 or housing is supported and manipulated by the robot 100 about the perineal skin surface 5 and the pneumatic stepper motor 180 is secured in the case. The pneumatic stepper motor 180 turns a nut 186 that engages a screw, formed by screw thread 721 made on the outer side of the first pneumatic cylinder 720*a*, in a controlled linear motion which is used to set the depth of needle insertion. The coaxial design of the first and second pneumatic cylinders 720*a,b* is used for needle 702 and stylus 704 insertion within the prostate 7 as further described herein.

The needle 702 is connected to a piston 730*a* (needle piston) of the first cylinder 720*a*. Needle insertion is performed when the first cylinder 720*a* is pressurized in the port P2 740*a*, and vacuum is used to retract the needle back. The needle piston 730*a* is set in motion by regulated air pressure. Its motion is uncontrolled in position, but its limits of motion are set by the ends of the stroke. The needle piston 730*a* movement in a first direction stops on the front end of the first cylinder 720*a* which is precisely positioned by the pneumatic motor 180. The back stroke is variable depending on the position of the motor 180. The limit of the movement of the needle piston 730*a* in a second direction occurs when an end of the second cylinder 720*b* is stopped on the back face 712 of the case 710. This insures that for any depth of insertion, the needle 702 retracts above the skin, but not more than that. This also keeps the tip of the retracted needle 702 guided within the nose 714 of the case 710.

In alternative embodiments, and with reference also to FIGS. 5(*c*),(*d*), the needle delivery apparatus 700 also is configurable so the needle piston 730*a* is moved in any of the first or second directions using any of a number of techniques known to those skilled in the art as well as combinations of more than one technique. For example and with reference to FIG. 5(*c*), the first cylinder 720*a* is configured with two pneumatic ports 740*a,b*. In this embodiment, needle insertion is performed when the first cylinder 720*a* is pressurized in the port P2 740*a* and needle withdrawal is performed when the first cylinder 720*a* is pressurized in the other port 740*b*. In either case, it is preferable that the portion of the chamber within the first cylinder 720*a* (i.e., the portion on the opposite side of the needle piston 730*a* from the port which is being pressurized) is vented.

In yet another exemplary embodiment and with reference to FIG. 5(*d*), one or more resilient members 770*a,b* are disposed within the cylinder and are arranged so as to one of extend or compress when the needle piston 730*a* moves in the first direction. Such resilient members are of materials that are image compatible. In one case, the resilient member 770*a* is located between a first end of the first cylinder 720*ac* and the needle piston 730*a* so that when the needle piston is moved in the first direction by pressurizing the port P2 740*a* the resilient member 770*a* is compressed there between. When the port P2 740*a* is vented and/or a vacuum is applied, the restoring force of the resilient member 770*a* moves the needle piston 730*a* in the second direction.

As also shown in FIG. 5(*d*), alternatively or in addition a resilient member 770*b* is located between a second end of the first cylinder 720*ac* and the needle piston 730*a* and also so that one end of the resilient member is secured to the needle piston and so another end thereof is secured to the first cylinder (e.g., second end thereof) or other structure of the needle delivery apparatus. Thus, when the needle piston 730*a* is moved in the first direction by pressurizing the port P2 740*a* the resilient member 770*b* is elongated there between. When the port P2 740*a* is vented and/or a vacuum is applied, the restoring force of the resilient member 770*b* moves the needle piston 730*a* in the second direction.

The resilient member can be any of a number of structures, devices or materials known to those skilled in the art. Such resilient members includes springs of all types and shapes as well as bands, rings or blocks of materials that can compress or stretch (e.g., resilient band to elongate or a resilient ring that compresses).

As indicated above, the needle delivery apparatus 700 also includes a second cylinder 720*b* which is carried by the needle piston 730*a* and which is moveably disposed within the first cylinder 720*a*. In illustrated exemplary embodiments, a portion of the second cylinder 720 also extends outwardly from a through aperture in the first cylinder 720*a*. As indicated above, movement of the needle piston 730*a* in the second directions is stopped when an end of the second cylinder, which is in the portion which extends outwardly, contacts the case 710.

The second cylinder 720*a* also includes a piston (stylet piston 730*b*) which is coupled to a stylet 704, which stylet piston is movable with the second cylinder. Stylet motion is pressure/vacuum actuated from port P1 742 in a similar fashion as that described above for the needle 702. The full stroke of the needle piston 730*b* pulls the stylet 704 all the way out of the needle 702. As also described above, any of a number of techniques known to those skilled in the art (e.g., a resilient member), can be adapted for use in the present invention to move the stylet piston in the second direction. As described further herein, the stylet is particularly usable when the needle delivery apparatus 700 is configured to deliver brachytherapy seeds 20.

Two fiber optic circuits are used to confirm the actions of the pneumatic cylinders. These are implemented with D10 Expert fiber optic sensors (Banner Engineering Corp., Minneapolis, Minn.). These sensors measure the intensity of the light beam passing between two ends of their fibers. The ends of the first sensor 760*a* are located on the back wall 712 of the housing 710. When retracted, the first cylinder 720*a* interrupts the light beam confirming that the needle is retracted. The second sensor 760*b* is located in the seed loading region. Depending on the positions of the pistons, this sensor can confirm that the stylet 704 has been retracted or the lowered drawer 752 contains a seed 20.

When the needle delivery apparatus 700 includes a seed deployment and reloading mechanism 750, such a seed deployment and reloading mechanism includes a seed delivery drawer 752 with a seed pocket, a seed delivery port P4 754 and a pressure port 756. In general, seeds 20 are brought from the control cabinet one at a time using pneumatic pressure through a thin hose connected to the a seed delivery port P4 754. When commanded, the seed 20 is loaded in the pocket of the drawer 750 through the port P4 754. When also commanded the drawer is lowered so the seed is effectively located in the lumen of the needle. Thereafter, the stylet 704 is moved in the first direction thereby pushing the seed through and out the needle 702. All seeds 20 are delivered with the same needle 702, one at a time, several for each needle insertion. Such seed delivery can be accomplished without spacers placed between the seeds or with spacers between the seeds. The present invention also features a seed loading or delivery apparatus that is discussed below in connection with FIG. 6, which can supply such seed to the seed deployment and reloading mechanism 750.

The needle delivery and seed delivery process is more particularly described as follows. First, the maximum depth of insertion for the needle 702 for a given trajectory is set by the pneumatic motor 180 of the needle delivery apparatus 700. The needle 702 is inserted at the target by pressurizing the appropriates port P1 742 and port P2 740a. Vacuum in port P1 742 pulls the stylet 704 all the way out of the needle 702 so that the point of the stylet clears the opening of the seed delivery drawer 750. A seed 20, which was preloaded shortly before, is brought down to the center of the needle 702 (i.e., in the needle lumen) by pressurizing port P3 756. Pressure in port P1 742 is then used to insert the stylet 704 into the needle lumen, thereby pushing the seed 20 through the needle 702 and deploy it at the needle tip 703. Preferably, this is done with a slow motion of the stylet 704 so as to prevent air buildup at the tip 703 of the needle 702. The speed of the stylet 704 is restricted with a flow valve proximally located.

The needle 702 is then backed up with the motor 180 to the location of the next region where a seed 20 is to be deployed and the above seed delivery process is repeated. In this way, a seed 200 can be deployed without requiring a spacer. The cycle then repeats by loading a new seed and retracting to the next location. When all seeds have been deployed on a direction, the robot 100 repositions the delivery apparatus 700 and the above described seed delivery process is repeated.

In exemplary embodiments, a needle delivery apparatus 700 configured for seed delivery embodies an 18G MRI compatible brachytherapy needle that can deploy seeds at depths 25 mm to 125 mm as the needle 702. A rendering of the pro/E design is presented in FIG. 5(a). As with the robot, all components of the needle delivery apparatus 700 are made of multi-imager compatible materials and the needle delivery apparatus 700 is electricity free, all actuation being performed pneumatically controlled by servo-valves located in the control unit 610 as described above.

Figure 7:
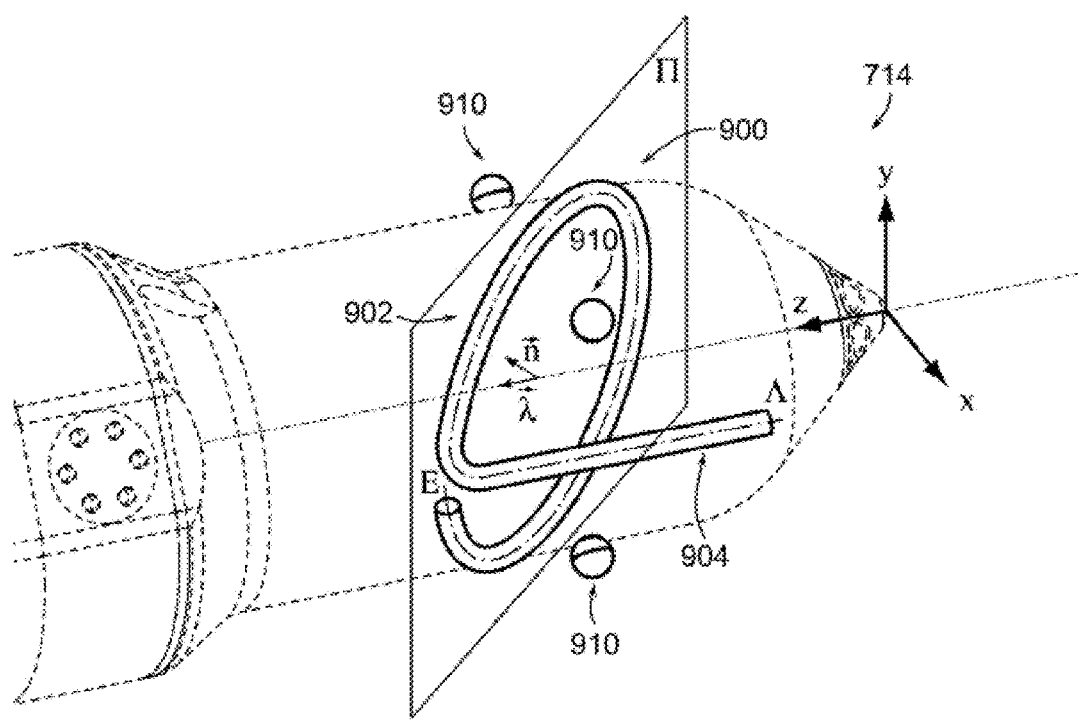

Referring now to FIG. 7, there is shown an illustrative schematic view of a seed delivery apparatus 800 according to another aspect of the present invention that is preferably used with the needle delivery apparatus 700 so that seeds are automatically delivered to the needle delivery apparatus and automatically injected therefrom into the tissue. According to preferred aspects of the present invention, the seed delivery apparatus 800 is located remote from the imager and in particular embodiments is located in proximity to the control unit 610 for the robot. In contrast to the present invention, traditionally brachytherapy seeds are preloaded in multiple needles or stored in a manually-operated seed magazine that mounts on the needle.

Also according to other aspects/embodiments of the present invention, the seed delivery apparatus 800 includes one or more seed delivery subsystems $802a,b \ldots n^{th}$ so that one or more types of seeds 20 (e.g., seeds having I-125, Pd-103) can be stored and delivered by the seed delivery apparatus. This, allows for increased dosimetry flexibility and the seed delivery apparatus 800 also is operable that so that either one of the seeds 20 can be loaded at any time. In addition to seed storage, it also is contemplated that one of the sub-systems can be loaded with spacers.

As describe below and with reference to FIG. 8(c), the seed delivery apparatus 800 embodies a microcontroller 810 that controls each of the one or more seed delivery subsystems 802 a,b including functionalities of each sub-system, so that the seeds 20 are delivered one at a time through a hose 804 or tubing interconnecting the seed delivery apparatus 800 and the needle delivery apparatus 700.

Each of the sub-systems 802 a,b includes a seed magazine (SM) 820, where seeds of the same type are loaded therein in, The seed magazine 820 essentially forms a jar, whose bottom is funnel shaped to facilitate the passage of the seeds into a sub-system delivery hose 820 (e.g., hose, tubing or thin pipe). If the seeds 20 become blocked, the seed magazine 820 is finely vibrated with a mechanical shaker 830 actuated by a motor (M) 832. From the seed magazine, the seeds 20 enter the sub-system delivery hose 820 and pass through a series of optical sensors and gates for monitoring, individual release, and counting as described further below.

As indicated above, the seed delivery apparatus includes a microcontroller (MC) 810 that controls the seed delivery apparatus 800 and each of the one or more sub-system 802a,b thereof. When a command is received to deliver a seed from the system controller 610 (FIG. 5(a)), the microcontroller 810 determines which sub-system a seed is to be delivered from and then the MC outputs a commands/signals to the functionalities of the applicable subsystem. In the illustrated embodiment, the MC 810 outputs commands/signals to a latch D1 840 to hold the column of seeds 200 above, and activates the drawer of the latch D2 842 to align the hole in the drawer with the seed above allowing it to pass. Air pressure P2 is applied above the seed by opening the valve V2 850. Consequently, one seed 20 is pushed out through the output hose 804. As it leaves the seed delivery apparatus 800, the seed 20 is counted with the optical sensor O3 860. Thereafter the latch D2 842 is closed, valve V2 850 is closed, and latch D1 840 is opened allowing the next seed 20 in the queue to advance to latch D2 842. This method of gating is tolerant in seed length variability.

The MC 810 also monitors the length of the seed queue with the optical sensor O1 862 and optical sensor O2 864. In particular embodiments, if the MC 810 determines that the queue level is at or below the optical sensor O2 864, then the MC outputs command/signals activating the shaking motor 832 thereby shaking the seed magazine 820. The MC 810 outputs commands/signals stopping the shaking motor 832 when it determines that the level of the seed queue is at or above the optical sensor O1 864. In this way, the MC 81 controls each of the sub-systems so that a column of seed 20 is always available for loading. The seed delivery system 600 is typically arranged so that the force of gravity causes seeds to pass from the seed magazine 820 to the output hose 804. This movement or passage is further aided by pressurizing the seed magazine 820 with pressure P1 by opening valve V1 852. Externally, the MC 810 takes "send one seed from magazine A, B, C, . . . " commands from the system controller 610 and makes its states and seed counters available for reading. In further embodiments, the seed delivery apparatus 800 is encased in lead and the seed travel circuit or pathway is sterilized with gas.

It also is within the scope of the present invention to adapt the seed delivery apparatus 800 so it can be used for other applications. For example, the seed delivery apparatus 800 is adaptable so as to as automatically preload the needles under computer controlled dosimetry planning, and have confirmation that the exact number and order of the seeds has been loaded. As indicated above the needle delivery apparatus 700 of the present invention can be operated so that seed spacers are not required. The seed delivery apparatus 800 of the present invention is adaptable so that one of the sub-systems 802 thereof to be configured to deliver seed spacers so that such seed spacers are alternatively deployed between the seeds 20.

Referring now to FIG. 7, a frontal portion of an end effector, such as the frontal part of a needle delivery apparatus 700 of the present invention, is configured so as to include a registration or geometry marker 900 that is used to register the robot 100 in the image space of CT or MRI scanners. The frontal part is selected because of its proximal location to the intervention site and so that the marker 900 is in or in close reach of the imaging field.

The registration marker 900 comprises an ellipse E 902 and a line A 904. The ellipse 902 is generated at the intersection of a cylinder (about the outer surface of the injector) with a plane π, as presented in the figure. The line 904 is located on the cylindrical surface and thus is parallel to the z axis of the robot. The plane π is parallel to the axis y of the robot 100 and makes an angle 45° angle with the xy robot plane. The registration marker 900 is implemented with a round cross section tube filled with MRI/CT contrast material. The marker's cross section preferably is round, so that the centroid of its image is the marker's center (E or A) for any angle of the slices. This has the advantage that when imaged, the tubes's image centroid shows the marker's center.

The marker is intersected by an MR or CT slice in one point λ of the line 904 and two points $\varepsilon=(\varepsilon^1,\varepsilon^2)$ of the ellipse 902. The points acquired over multiple slices of the marker (i≥2) form two sets of points $\lambda_i$ and $\varepsilon_i$. Points $\lambda_i$ are used to estimate the equation of the line in image coordinates $\Lambda^I$. Similarly points $\varepsilon_i$ estimate the plane $\pi^I$. The transformation of coordinates is calculated based on the $\Lambda$, $\Lambda^I$ and $\pi$, $\pi^I$ representations of the same objects in the two spaces, as follows:

The rotation of the two spaces is computed using the direction $\overline{\Lambda}^I$ of the line $\Lambda^I$ and the normal direction $\overline{n}^I$ of the plane $\pi^I$. The y axis of the robot in image coordinates is $\overline{y}^I = \overline{n}^I \times \overline{\Lambda}^I$. The direction of the $\overline{y}^I$ vector is chosen to point in the direction of the corresponding image coordinate. The robot to image rotation matrix is calculated as:

$$R = [\overline{y}^I \times \overline{\Lambda}^I \overline{y}^I \overline{\Lambda}^I]$$

The translation component is computed based on the line-plane intersections, as:

$$T = [\Lambda^I \cap \pi^I] - R[\Lambda \cap \pi]$$

As such, the image coordinates of a robot space point P are:

$$P^I = RP + T$$

The frontal portion of the needle delivery apparatus 700 also is configurable to as to include an additional set of point markers 910 (e.g., 4 point markers) that are placed at precise locations on the outer surface of the frontal portion, as shown in FIG. 7. In exemplary embodiments, these point markers 910 are represented by contrast filled spheres. These point markers are usable to assess the accuracy of the above registration algorithm by verifying that their images match their preset location.

Figure 8A:
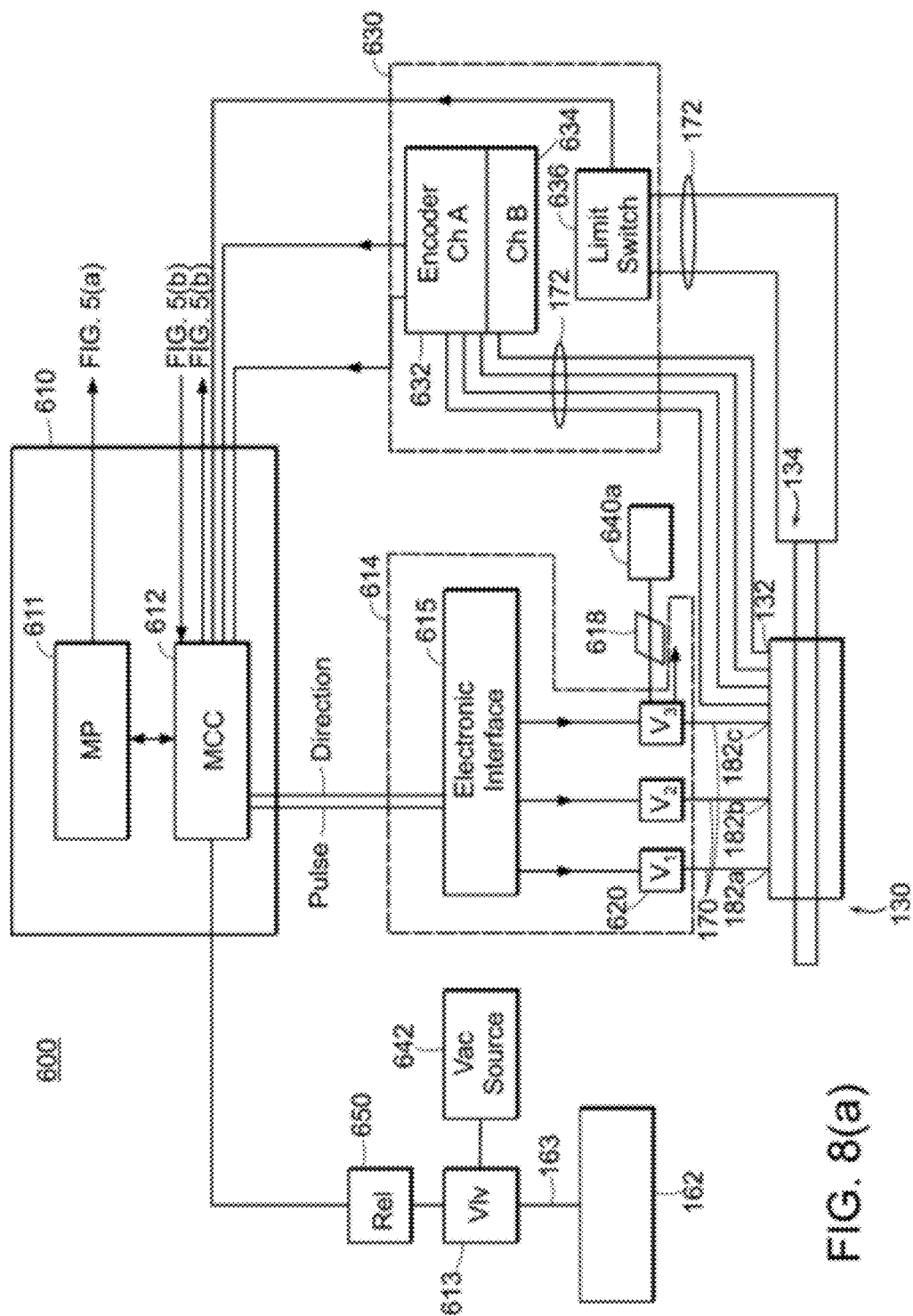
FIG. 8(c) is a schematic block diagram view of a seed delivery apparatus of the present invention for one subsystem illustrated for clarity.
Figure 8B:
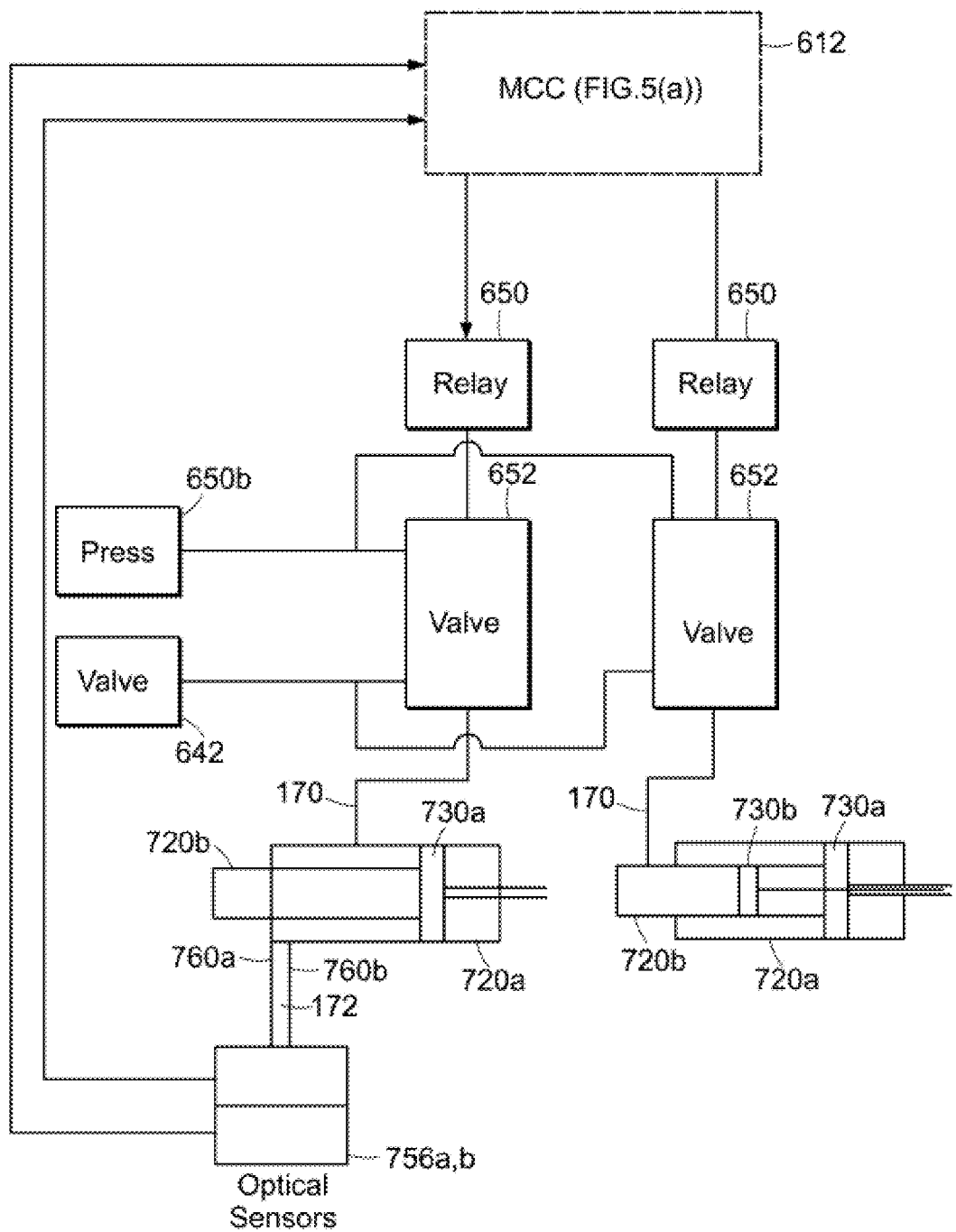
Figure 8C:
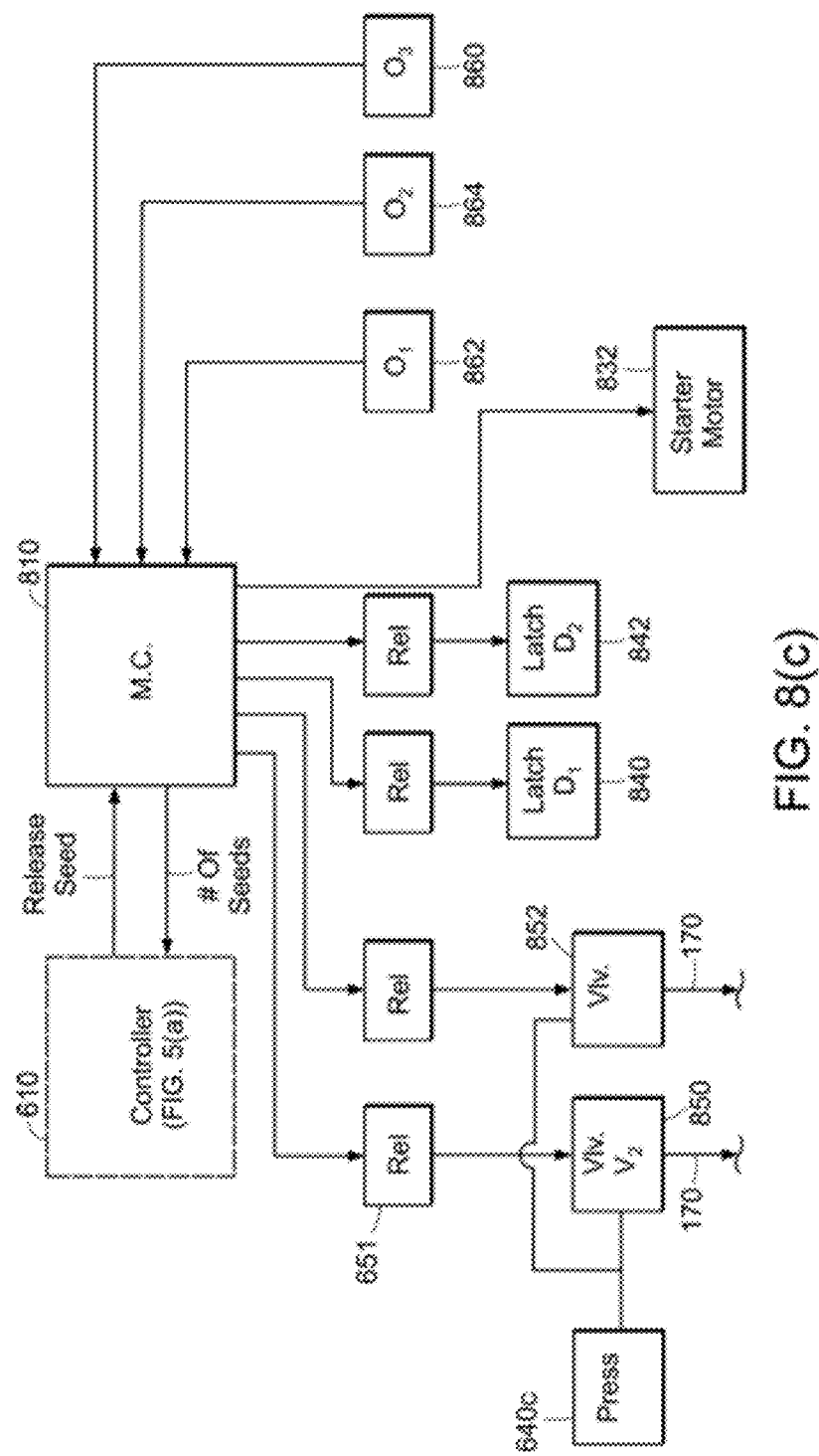

Referring now to FIGS. 8(a)-(c) there is shown a schematic block diagram view of a robotic system 600 of the present invention (FIG. 8(a)), a schematic block diagram view when the robotic system further includes a needle delivery apparatus 700 of the present invention (FIG. 8(b)) and a schematic block diagram view when the robotic system further includes a seed delivery apparatus 800 of the present invention (FIG. 8(c)). Referring now to FIG. 8(a), the robotic system 600 includes a robot 100 with and end effector 200 and a system controller 610 or control unit. The system controller 610, which can be implemented in the form of a control cabinet, is remotely located outside the imager's room, either in the control room of the imager or other space. The robot 100 is connected to the system controller 610 by a bundle of tubing, hoses or fluid lines 170 and fiber optic cables 172. This allows for all non-MRI compatible materials, electric and magnetic components to be located outside the MRI field. In exemplary embodiments length of the fluid lines 170 and the fiber optic cables 172 is about 6 m. Reference also should be made to FIGS. 2(a), 4 and 5(a),(b) for functionalities and details not otherwise shown on FIG. 8(a).

The system controller 610 includes a personal computer as is known in art, including a microprocessor, RAM, storage mediums, display(s) and one or more applications programs for execution on the personal computer. The system controller 610 also includes one or more motion control cards (MCC) 612 that each includes one or more application programs for execution on the MCC. Typically, the MCC would be located within the cabinet housing the personal computer and operably coupled to the personal computer. For example, the MCC 612 would be operably coupled to the mother board on which is mounted the microprocessor and RAM. For simplicity and clarity, one control and one sensing channel for one actuator 130 of the robot 100 is shown in FIG. 8(a) and described below. It should be recognized, however, that for a robot 100 such as that shown in FIGS. 2(a)-(b), there would be five of such control and sensing channels.

In an exemplary embodiment, the microprocessor is a dual-processor industrial personal computer equipped with a motion control card 614 (e.g., MC-8000, 8-axis PCI-DSP by PMDI, Victoria, BC, Canada). The motion control card 614 performs all control tasks, from the low level motion control of the actuators to the image registration and image-guided control algorithms. More particularly, an application program is provided which includes instructions, criteria and code segments for performing such control tasks. In this regard, it should be recognized that it is well within the skill of those knowledgeable in the programming arts to develop such instructions, criteria and code segments for performing such control tasks.

As indicated above, each of the pneumatic motors 180 is set in motion by sequentially pressurizing its pneumatic ports 182 such as for example in a 6-step pneumatic commutation process. Thus, the robotic system 600 also includes an electro-pneumatic interface 614 and a common manifold of a plurality of valves 620 (e.g., 18 valves when the motor includes three pneumatic ports 182 and the robot includes 5 motors180/actuators130 and the needle delivery apparatus 700 includes 1 motor). The electro-pneumatic interface 614 is implemented with valves 620 (e.g., direct-acting solenoid valves; NVKF334V-5D by SMC Corp., Indianapolis, Ind.) and an electronic interface 615 that includes circuitry arranged to control the valves with standard electric stepper-motor motion-control cards installed in the system controller unit 610. In further embodiments, the air is supplied by a pressure source 640 to the manifold and is regulated by an electronic regulator 618. The electronic interface 615 directionally cycles the activation of the valves in the desired 6-step sequence, as controlled by the step and direction signals of the motion control card 614.

The control unit 600 also includes an electro-optical interface 630. In an exemplary embodiment, the electro-optical interface 630 is implemented with fiber optic sensors (e.g., D10 Expert fiber optic sensors, Banner Engineering Corp., Minneapolis, Minn.). Three of these sensors are used for each motor 180, two sensors 632, 634 for measuring incremental rotary motion with quadrature encoding, and one sensor 636 as a limit-switch for zeroing linear motion. These are used as feedback in closed loop control of the pneumatic stepper motor 180, to ensure that the motor is not skipping steps and IGI motion is executed as prescribed.

In the case of the five motors 180 for the robot linear actuators 130, the control signals (pulse and direction) cause the linear actuators to move in the desired fashion to orient the platform 120 and thus, the end effector 200 for the desired orientation with respect to the target area. As to the motor 180 of the needle delivery apparatus 700, the control signals (pulse and direction) cause the motor to move the first cylinder 720*a* in either the first or second directions and so as to set the depth of insertion of needle.

As indicate above, the robot 100 is configurable with suction cup structures 162 that removably couple the robot to the support structure. In further embodiments, the robotic system 600 further includes a relay 650 and a valve 613. The valve is selectively, fluidly coupled to a vacuum source 642 and the suction cup structures 162 by tubing 163. In use, the MCC 612 outputs a signal to the relay 650 which in turn outputs a signal to the valve causing the valve to open or close, thereby coupling or decoupling the vacuum source 642 and the suction cup structures 162.

Referring now to FIG. 8(*b*), there is shown the control circuitry and logic associated with the needle delivery apparatus 700 of the present invention excluding that for the motor 180 which is described above. Reference also should be made to FIGS. 7(*a*),(*b*) for functionalities not otherwise described below and/or not shown on FIG. 8(*b*).

When configured with the needle delivery apparatus 700, the robotic system 600 further includes a plurality of valves 652; a plurality of relays 650, one relay for each valve; a pneumatic pressure source 640*b*, and a vacuum source 642. The valves are coupled to the inlet ports on the first and second cylinders by fluid lines 170 and optical sensors on the first and second sensors are coupled to the MCC via fiber optic cables 172. The MCC 612 is shown in phantom on this figure as it is the MCC also shown on FIG. 8(*a*).

The relays 650 are electrically coupled to the valves 652 and the motor control card 612 (FIG. 8(*a*). Each valve is preferably a two-way valve that selectively couples its output to one of two inlets, where the two inlets are coupled respectively to the pressure source 640*b* and the vacuum source 642. In use the MCC 612 outputs a signal to the appropriate relay 650 to connect the valve 652 to the pressure source 640*b* when the cylinder is to be pressurized to move the needle piston 730*a* and/or the stylet piston 730*b* in the first direction and to the vacuum source when it is desired to move the needle piston or the stylet piston in the second direction. The MCC 612 also is operably coupled to the optical sensors 756*a,b* that provides an electro-optical interface for the sensors 760*a,b*.

Figure 6:
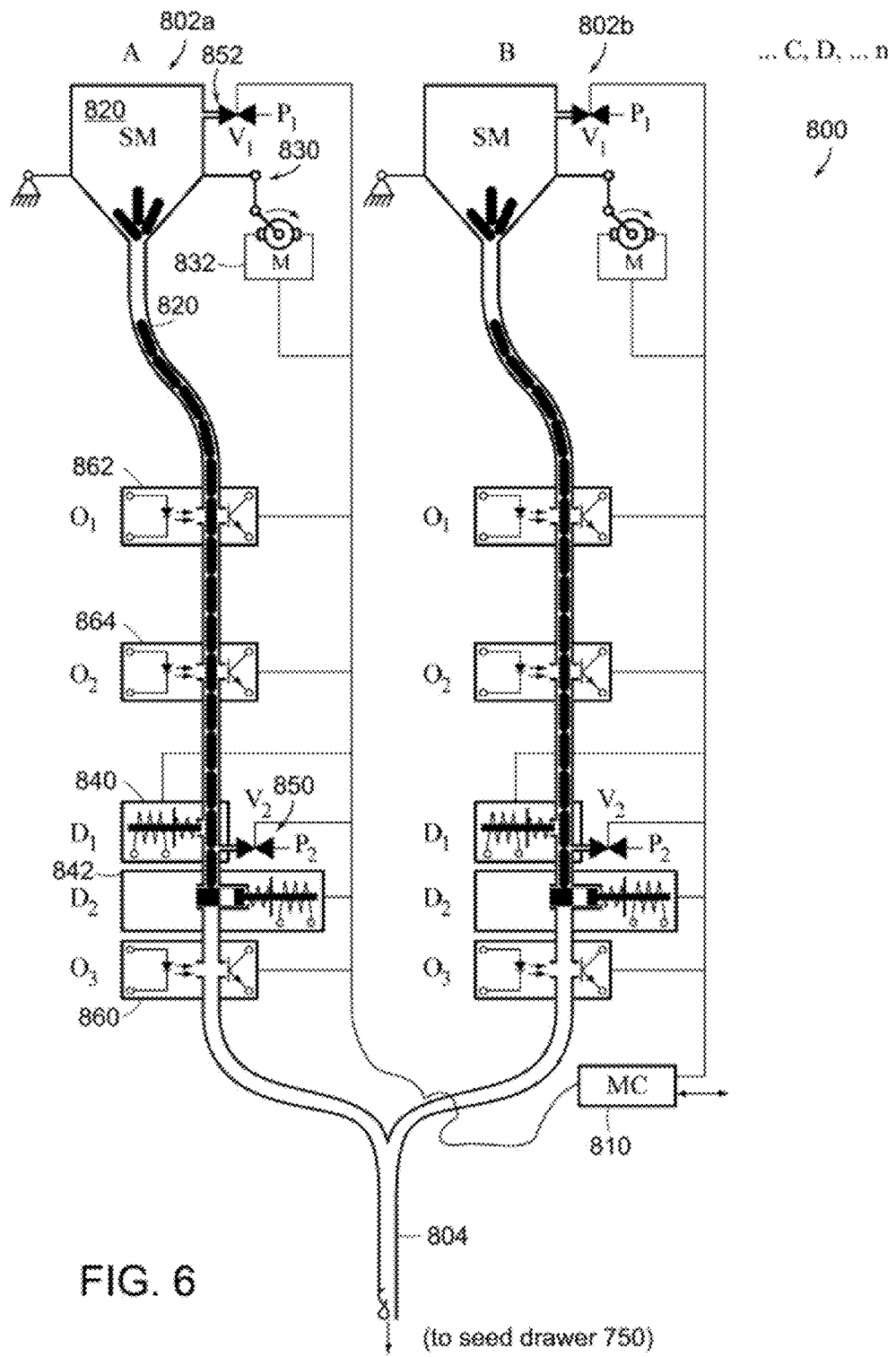

Referring now to FIG. 8(*c*), there is show the control circuitry and logic associated with the seed delivery mechanism 700. Reference also should be made to FIG. 6 for functionalities not otherwise described below and/or shown on FIG. 8(*c*).

When configured with the needle delivery apparatus 700, the robotic system 600 further includes a plurality of relays 651 and a pneumatic pressure source 640*c*. The microcontroller 810 is configured so as control the seed delivery mechanism such that there is a supply of seeds 20 in a queue for each sub-system 802*a, b* and to cause signals to be outputted when such a queue is not available. Microcontroller 810 also is operably coupled to the control unit 610, more particularly the microprocessor 611 thereof, so as to be responsive to commands from the control unit 610 directing that a seed of a particular type be delivered as well counting the seeds being delivered and inputting this information to the controller. Although the MC 810 is shown as a separate element, it should be recognized that the operation of the seed controller can be implemented by the microprocessor 611, the MCC 612 or another control card operably coupled to the microprocessor 611 within the control unit.

The relays 651 coupled to the valves 850,851 are operated by the MC 810 so as to provide a voltage signal to each of the valves to selectively open to a pressure source 640*a* or to isolate the tubing of the seed delivery mechanism from the pressure source. In similar fashion, the relays coupled to the latches 840, 842 provide a voltage signal to operate the latch so as to open and close the latch as is described above in connection with FIG. 6. The relays 650, 651 are any of a number of electrical devices known to those skilled in that art that are actuated by a signal output from a control device (e.g., a microcontroller or control card) and which generate a output at a desired voltage required to operate another device connected thereto.

As described above, the seed delivery mechanism include three optical sensors 860, 862,864, which provide an output signal. These optical sensors 860-864 are electrically operably coupled to the microcontroller 810 so as to carry out the functions described above in regards to FIG. 6. The optical sensors are any of a number of sensors known to those skilled in that art that can carry out the functions described above.

Motion Imager and Compatibility Tests

Figure 9B:
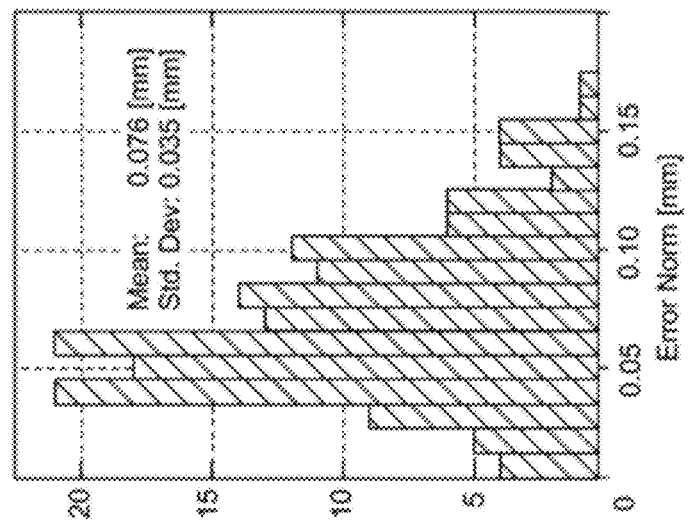
FIG. 9(b) is a histogram of the error's norm.
Figure 9A:
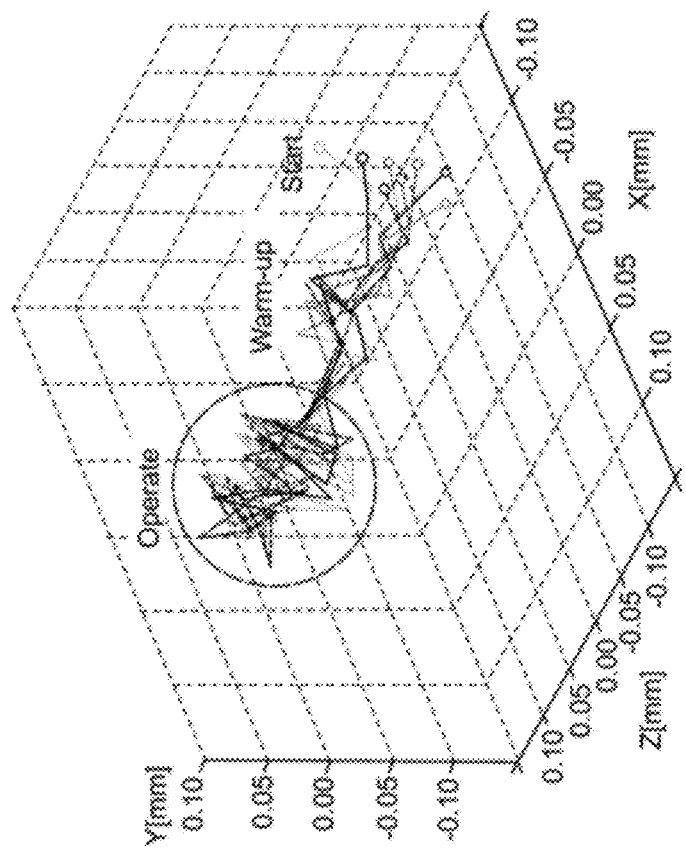
FIG. 9(a) is graphical view of positioning repeatability errors.

Two initial tests were performed to assess the basic motion capabilities and multi-imager compatibility of the robot 100 of the present invention. In the motion tests the robot 100 was commanded to sequentially position in 8 extreme points of the work space. Each cycle was then repeated 20 times. An optical tracking system (Polaris, NDI, Ontario, Canada) was used to measure the actual position of the robot 100 with an active 6 DOF marker mounted on the robot's platform 120 (FIG. 2). In order to reduce measurements errors, each position was averaged over 10 data acquisitions with the robot 100 at rest Positioning repeatability errors were then plotted as represented in FIG. 9(*a*). This shows that after a warm-up phase the errors settle around 0.050 mm.

The histogram in FIG. 9(*b*) shows that the mean value of the error's norm over all the experiments was 0.076 mm with a standard deviation of 0.035 mm. A similar motion repeatability experiment was performed with the robot 100 positioned within a 1.5 T MRI scanner, to see if motion is influenced by the magnetic field. The results show a mean value of 0.060 mm and standard deviation of 0.032 mm. These somewhat better results achieved in the MRI were explained due to several unrecorded warm-up cycles performed while adjusting the robot 100 within the confined space of the scanner. In addition, these results incorporate measurements errors, so the actual values of robot repeatability are actually lower.

Figure 10A:
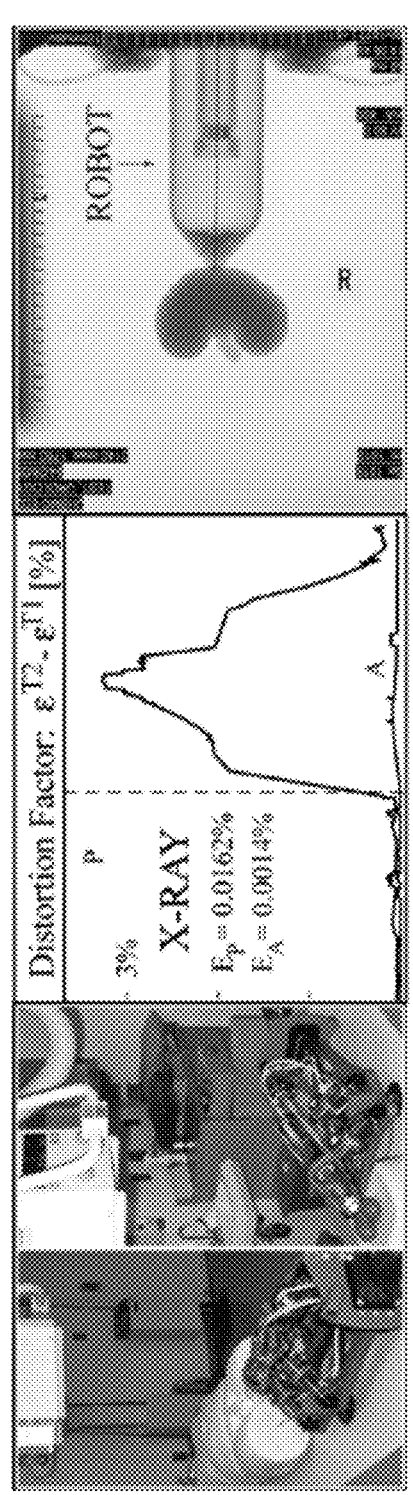
FIGS. 10A-10C are various views of image compatibility tests when using the robot and systems of the present invention.
Figure 10B:
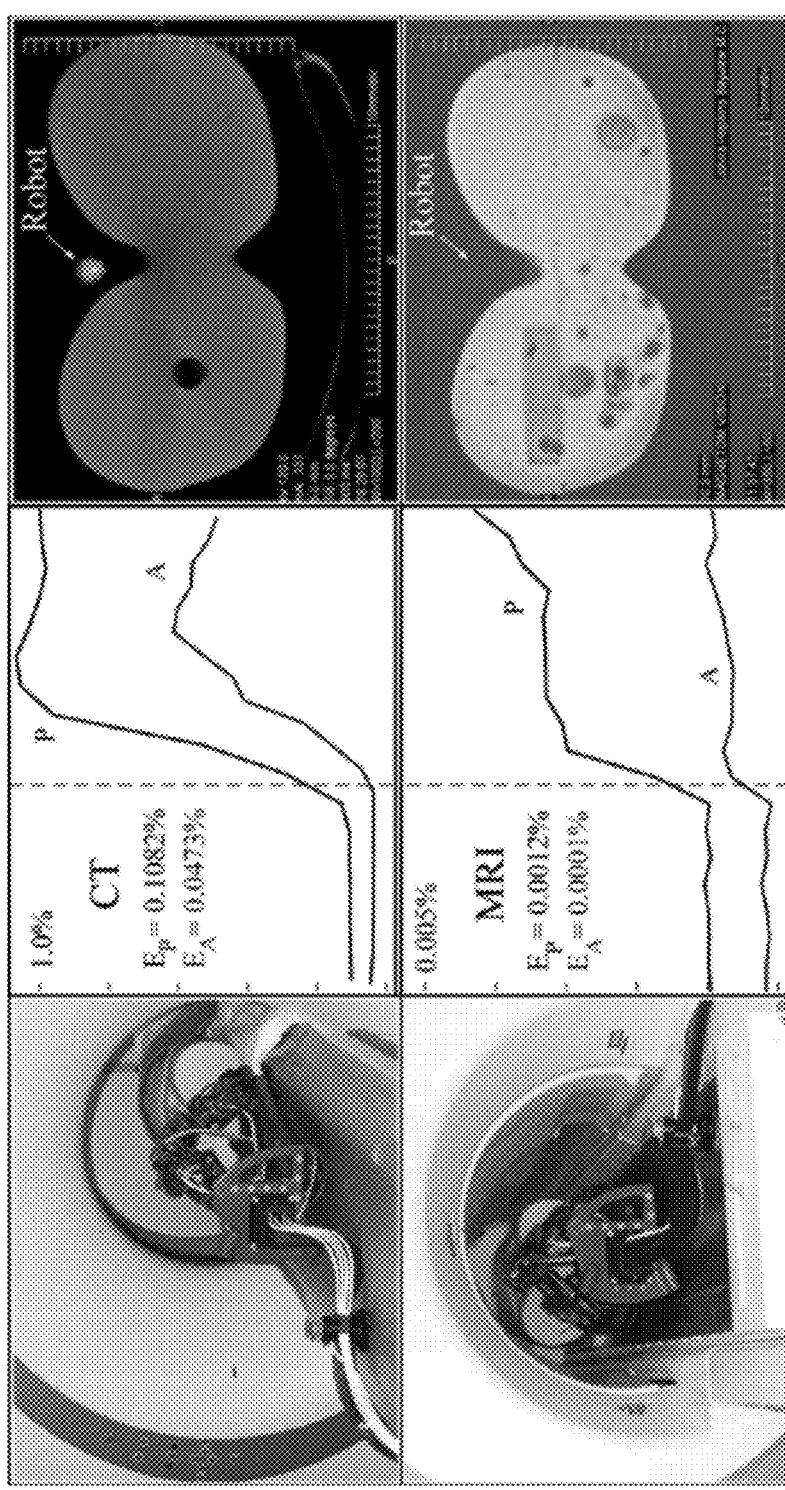
Figure 10C:
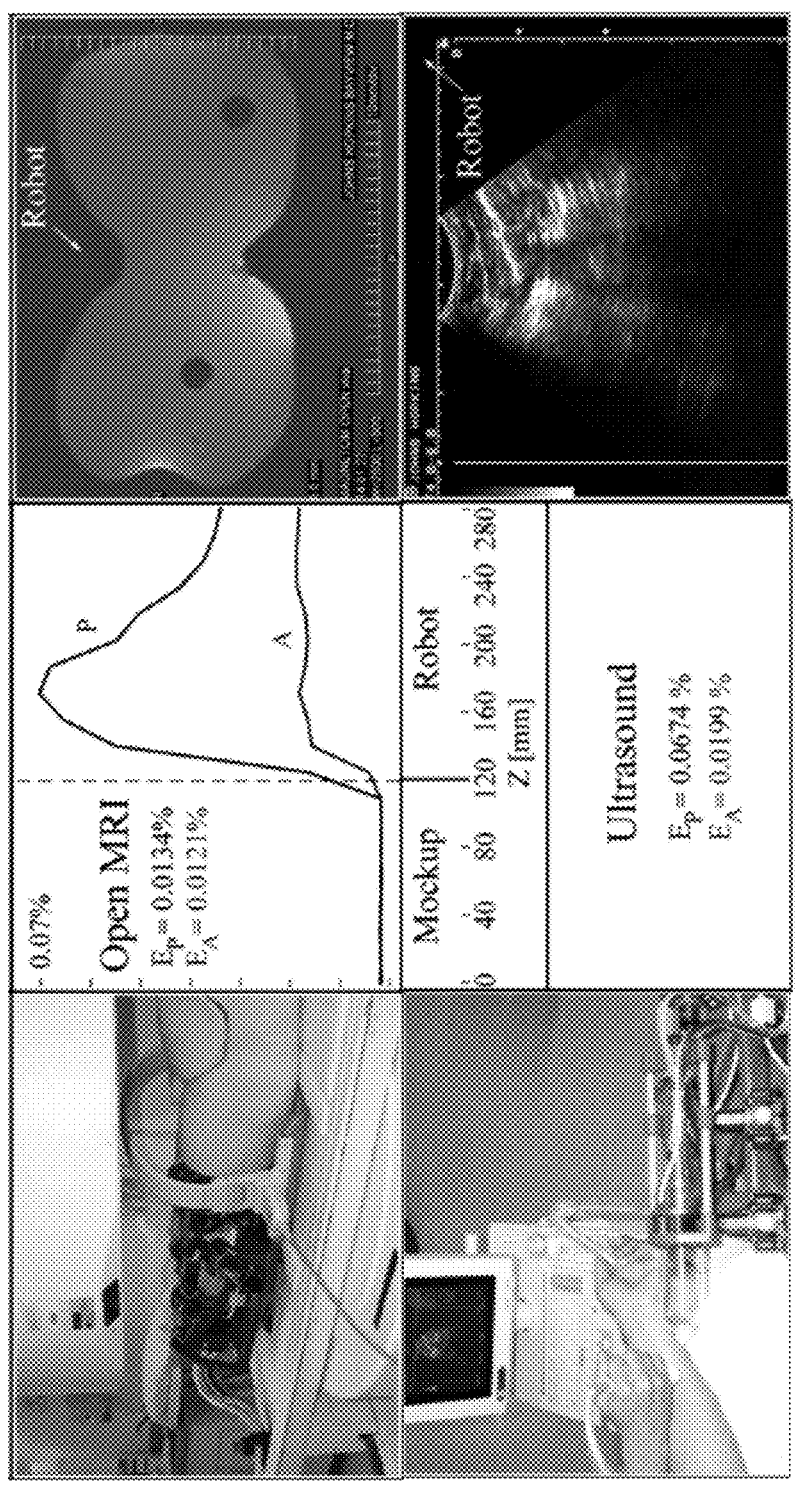

Imager compatibility tests also were performed with the robot 100 in all classes of imaging equipment. There is shown in FIG. 10 five sets of experiments performed under X-Ray, CT, Closed MRI, Open MRI, and Ultrasound (in rows). For each experiment the figure presents a photograph of the setup, a graph, and an image of the respective dataset (in columns). A human torso mockup, a kidney model, and an arm were used in the experiments. Tests were performed according to a multi-imager compatibility method, in which difference imaging ($\in^{T2}-\in^{T1}$) is involved to show the level of image distortion due to the presence of the robot in the imager field (P-passive), as well as its activation (A-active). The P graphs plot a mean measure of the pixel value differences between images taken with ($\in^{T2}$) and without ($\in^{T1}$) the robot versus a coordinate measuring the distance between the mockup and the robot. The A test is similar, but the differences are taken between images with and without robot motion. The low levels of imaging errors in the left side of the graphs (Mockup side) show that the presence and activation of the robot during imaging does not affect image quality in the region of interest (where the IGI site is). The right sides of the graphs (Robot side) show if the robot 100 is visible or not in the medical image. These graphs and the medical images in the right column show that the robot 100 is visible in X-Ray based imagers, but is translucent under MRI and ultrasound. $E_P$ and $E_A$ percent coefficients give an integral measure of the graphs in the mockup region. These very low coefficients show that the robot 100 does not create image artifacts even if operated during imaging in any class of imaging equipment. Coefficients $E_P<1\%$ and $E_A<0.5\%$ were associated by experienced radiologists with minimal or unperceivable artifacts.

The results of the imager tests performed with the robot 100 in motion at or immediately near the imaging region in all classes of imaging equipment show that the robot is multi-imager compatible. This is a new achievement for MRI compatibility since previous robots (i.e., piezo-operated) had to be disabled during imaging and positioned away from imaging regions.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A robot for image-guided interventions, comprising:
a base member;
a platform; and
exactly five linear actuators connected in parallel between the base member and the platform, the linear actuators, the base member, and the platform being arranged so that the platform is moveable with respect to the base member, wherein
the linear actuators provide five degrees of freedom of movement of the platform relative to the base member and obstruct one degree of freedom of movement of the platform relative to the base member by preventing rotation of the platform about an axis of a needle,
one of the five linear actuators obstructs the one degree of freedom of movement by preventing the rotation of the platform about the axis of the needle,
the one linear actuator is operatively coupled to the base member and the platform, respectively, by two end joints of the same type, and
the remaining four linear actuators are each operatively coupled to the base member by a first end joint and each operatively coupled to the platform by a second end joint, the first end joint being a U-joint, and the second end joint being a spherical joint.

2. The robot of claim 1, wherein each of the linear actuators includes a pneumatic motor for moving the platform with respect to the base member.

3. The robot of claim 2, wherein the pneumatic motor further includes a gear head that converts rotary motion of the motor to linear movement along an axis of the actuator.

4. The robot of claim 3, wherein the gear head includes a nut and a screw mechanism.

5. The robot of claim 1, further comprising fiber optic cables optically interconnecting a fiber optic encoder and a limit switch to electro-optical interface elements that detects light beam interruptions caused by designated moving elements in one or more of the linear actuators and provide electrical output signals therefrom, the optical cables having a length so that the electro-optical interface elements are located at least a predetermined distance from an imaging device.

6. The robot of claim 1, wherein at least a first pair of the linear actuators are coupled to a proximal portion of the platform, and at least a second pair of the linear actuators are coupled to the platform at a position distal to the first pair of linear actuators.

7. The robot of claim 1, wherein at least one of the linear actuators is coupled to the base member and positioned proximal to an end effector, and at least one other of the linear actuators is coupled to the base member and not positioned proximal to the end effector.

8. The robot of claim 1, wherein the linear actuators are interposed between end joints that connect to the base member and the platform, respectively.

9. The robot of claim 8, wherein one of the five linear actuators obstructs the one degree of freedom of movement by preventing rotation of the platform about a direction of linear motion of the one linear actuator.

10. The robot of claim 1, wherein at least one end joint connecting at least one of the linear actuators to the base member is disposed on a plane parallel to a portion of the base member, and at least one other end joint connecting at least one other of the linear actuators to the base member is not disposed on the plane parallel to the portion of the base member.

11. The robot of claim 1, wherein end joints connecting four of the linear actuators to the base member are disposed on plane parallel to a portion of the base member, and an end joint connecting the remaining one linear actuator to the base member is not disposed on the plane parallel to the portion of the base member.

12. The robot of claim 11, wherein the remaining one linear actuator obstructs the one degree of freedom of movement by preventing rotation of the platform about a direction of linear motion of the remaining one linear actuator.

13. The robot of claim 1, wherein a first section of the base member is perpendicular to a second section of the base member.

14. The robot of claim 13, wherein at least one end joint connects at least one of the linear actuators to the first section of the base member, and at least one other end joint connects at least one other of the linear actuators to the second section of the base member.

15. A robotic system comprising
a robot including:
a base member,
a platform, and
exactly five linear actuators connected in parallel between the base member and the platform, the linear actuators, the base member and platform being arranged so that the platform is moveable with respect to the base member; and
a control unit that is operably coupled to each of the linear actuators, the control unit being configured to control operation of the robot, wherein the linear actuators provide five degrees of freedom of movement of the platform relative to the base member and obstruct one degree of freedom of movement of the platform relative to the base member by preventing rotation of the platform about an axis of a needle, one of the five linear actuators obstructs the one degree of freedom of movement by preventing the rotation of the platform about the axis of the needle, the one linear actuator is operatively coupled to the base member and the platform, respectively, by two end joints of the same type, and the remaining four linear actuators are each operatively coupled to the base member by a first end joint and each operatively coupled to the platform by a second end joint, the first end joint being a U-joint, and the second end joint being a spherical joint.

16. The robotic system of claim 15, wherein each of the linear actuators includes a stepper motor for moving the platform with respect to the base member.

17. The robotic system of claim 16, wherein the stepper motor further includes a gear head that converts rotary motion of the stepper motor to linear movement along an axis of a particular linear actuator.

18. The robotic system of claim 16, wherein the stepper motor further includes a first moving element that is rotated responsive to the stepper motor's stepping motion and a second moving element that engages the first moving element so that the second moving element moves linearly along an axis of a particular linear actuator responsive to rotation of the first moving element.

* * * * *

UNITED STATES PATENT AND TRADEMARK OFFICE
CERTIFICATE OF CORRECTION

PATENT NO. : 10,315,046 B2
APPLICATION NO. : 12/085972
DATED : June 11, 2019
INVENTOR(S) : Dan Stoianovici et al.

It is certified that error appears in the above-identified patent and that said Letters Patent is hereby corrected as shown below:

In the Specification

Column 1, Lines 10-16, please replace with the following:
STATEMENT REGARDING FEDERALLY SPONSORED RESEARCH
This invention was made with government support under CA088232, awarded by the National Institutes of Health. The government has certain rights in the invention.

Signed and Sealed this
Twenty-second Day of August, 2023

Katherine Kelly Vidal
*Director of the United States Patent and Trademark Office*